United States Patent
Fini et al.

(10) Patent No.: US 10,398,755 B2
(45) Date of Patent: *Sep. 3, 2019

(54) CLUSTERIN PHARMACEUTICALS AND TREATMENT METHODS USING THE SAME

(71) Applicant: UNIVERSITY OF SOUTHERN CALIFORNIA, Los Angeles, CA (US)

(72) Inventors: M. Elizabeth Fini, Pasadena, CA (US); Shinwu Jeong, Buena Park, CA (US)

(73) Assignee: University of Southern California, Los Angeles, CA (US)

( * ) Notice: Subject to any disclaimer, the term of this patent is extended or adjusted under 35 U.S.C. 154(b) by 21 days.

This patent is subject to a terminal disclaimer.

(21) Appl. No.: 14/971,862

(22) Filed: Dec. 16, 2015

(65) Prior Publication Data

US 2016/0213747 A1     Jul. 28, 2016

Related U.S. Application Data

(60) Continuation of application No. 14/473,622, filed on Aug. 29, 2014, now Pat. No. 9,241,974, which is a division of application No. 12/814,349, filed on Jun. 11, 2010, now abandoned.

(60) Provisional application No. 61/186,724, filed on Jun. 12, 2009.

(51) Int. Cl.
| | |
|---|---|
| *A61K 38/17* | (2006.01) |
| *A61K 9/08* | (2006.01) |
| *A61K 9/00* | (2006.01) |

(52) U.S. Cl.
CPC ........ *A61K 38/1761* (2013.01); *A61K 9/0048* (2013.01); *A61K 9/08* (2013.01); *A61K 38/17* (2013.01)

(58) Field of Classification Search
None
See application file for complete search history.

(56) References Cited

U.S. PATENT DOCUMENTS

| | | | |
|---|---|---|---|
| 4,654,132 A | 3/1987 | Takagi et al. | |
| 6,075,122 A | 6/2000 | Cheever et al. | |
| 6,187,331 B1 * | 2/2001 | Itoh | A61K 9/0048 424/427 |
| 9,241,974 B2 * | 1/2016 | Fini | A61K 38/1761 |
| 2005/0043271 A1 | 2/2005 | Gross et al. | |
| 2006/0189514 A1 * | 8/2006 | Panjwani | A61K 38/1732 514/9.4 |
| 2008/0248526 A1 | 10/2008 | Mollat et al. | |

FOREIGN PATENT DOCUMENTS

| | | | |
|---|---|---|---|
| JP | 09227401 A | * | 9/1997 |
| JP | 2006335684 A | * | 12/2006 |
| WO | 2004084932 A2 | | 10/2004 |
| WO | 2008136547 A1 | | 11/2008 |

OTHER PUBLICATIONS

Alves et al. Dry eye disease treatment: a systematic review of published trials and a critical appraisal of therapeutic strategies. Ocul Surf. Jul. 2013;11(3):181-92.*
Mullins JD. "Ophthalmic Preparations," Chapter 87, in Remington's Pharmaceutical Sciences, 17th edition (Jun. 1985), Mack Pub. Co., Easton, Pennsylvania, pp. 1553-1566.*
NM_001831, GenBank Nucleotide Database [online], National Center for Biotechnology Information, U.S. National Library of Medicine 8600 Rockville Pike, Bethesda MD, 20894 USA. [retrieved on Jan. 19, 2017]. Retrieved from the internet<URL: https://www.ncbi.nlm.nih.gov/nuccore/NM_001831.3>.*
Pflugfelder et al. Matrix metalloproteinase-9 knockout confers resistance to corneal epithelial barrier disruption in experimental dry eye. Am J Pathol. Jan. 2005;166(1):61-71.*
Stern et al. Dry eye as a mucosal autoimmune disease. Int Rev Immunol. Feb. 2013;32(1):19-41.*
Bauskar et al; PLOS ONE, 2015, pp. 1-24.*
Human Clusterin (secretory form)[online], Aug. 13, 2007[retrieved Mar. 9, 2014]. Retrieved from Internet Archive Wayback Machine: <http://web.archive.org/web/20070813011014/http://www.adipogen.com/english/rp_product_view.asp?seq=205>.
Leskov et al. "Synthesis and functional analyses of nuclear clusterin, a cell death protein" J Biol Chem. Mar. 28, 2003; 278(13): 11590-11600. Epub Jan. 24, 2003.
Jones et al. "Clusterin" Int J Biochem Cell Biol. May 2002; 34(5): 427-431.

* cited by examiner

*Primary Examiner* — Bridget E Bunner
(74) *Attorney, Agent, or Firm* — DLA Piper LLP (US)

(57) ABSTRACT

Disclosed are pharmaceutical compositions comprising clusterin and polypeptides substantially the same as clusterin and treatment methods for inflammatory diseases and dry eye disease. The pharmaceutical compositions include an isolated clusterin or an isolated polypeptide substantially the same as clusterin. The clusterin is preferably secreted clusterin. The method of treating dry eye disease includes administering to a patient in need an effective amount of a pharmaceutical composition comprising an isolated clusterin or an isolated polypeptide substantially the same as clusterin. The method of treating a disease state characterized by inflammation includes administering to a patient having the disease state an amount of isolated clusterin or a protein substantially the same as clusterin effective to decrease the activity of a matrix metallproteinase selected from the group consisting of MMP-9, MMP-2 and MMP-7.

7 Claims, 10 Drawing Sheets

Specification includes a Sequence Listing.

A

B

SEQUENCE LISTING

```
<160> NUMBER OF SEQ ID NOS: 10

<210> SEQ ID NO 1
<211> LENGTH: 447
<212> TYPE: PRT
<213> ORGANISM: Homo sapiens

<400> SEQUENCE: 1

Met Met Lys Thr Leu Leu Leu Phe Val Gly Leu Leu Leu Thr Trp Glu
1               5                   10                  15

Ser Gly Gln Val Asp Gln Thr Val Ser Asp Asn Glu Leu Gln Glu Met
            20                  25                  30

Ser Asn Gln Gly Ser Lys Tyr Val Asn Lys Glu Ile Gln Asn Ala Val
        35                  40                  45

Asn Gly Val Lys Gln Ile Lys Thr Leu Ile Glu Lys Thr Asn Glu Glu
    50                  55                  60

Arg Lys Thr Leu Leu Ser Asn Leu Glu Glu Ala Lys Lys Lys Lys Glu
65                  70                  75                  80

Asp Ala Leu Asn Glu Thr Arg Glu Ser Glu Thr Lys Leu Lys Glu Leu
                85                  90                  95
```

```
Pro Gly Val Cys Asn Glu Thr Met Met Ala Leu Trp Glu Glu Cys Lys
            100                 105                 110
Pro Cys Leu Lys Gln Thr Cys Met Lys Phe Tyr Ala Arg Val Cys Arg
        115                 120                 125
Ser Gly Ser Gly Leu Val Gly Arg Gln Leu Glu Glu Phe Leu Asn Gln
    130                 135                 140
Ser Ser Pro Phe Tyr Phe Trp Met Asn Gly Asp Arg Ile Asp Ser Leu
145                 150                 155                 160
Leu Glu Asn Asp Arg Gln Gln Thr His Met Leu Asp Val Met Gln Asp
                165                 170                 175
His Phe Ser Arg Ala Ser Ser Ile Ile Asp Glu Leu Phe Gln Asp Arg
            180                 185                 190
Phe Phe Thr Arg Glu Pro Gln Asp Thr Tyr His Tyr Leu Pro Phe Ser
        195                 200                 205
Leu Pro His Arg Arg Pro His Phe Phe Pro Lys Ser Arg Ile Val
    210                 215                 220
Arg Ser Leu Met Pro Phe Ser Pro Tyr Glu Pro Leu Asn Phe His Ala
225                 230                 235                 240
Met Phe Gln Pro Phe Leu Glu Met Ile His Glu Ala Gln Gln Ala Met
                245                 250                 255
Asp Ile His Phe His Ser Pro Ala Phe Gln His Pro Pro Thr Glu Phe
            260                 265                 270
Ile Arg Glu Gly Asp Asp Arg Thr Val Cys Arg Glu Ile Arg His
        275                 280                 285
Asn Ser Thr Gly Cys Leu Arg Met Lys Asp Gln Cys Asp Lys Cys Arg
290                 295                 300
Glu Ile Leu Ser Val Asp Cys Ser Thr Asn Asn Pro Ser Gln Ala Lys
305                 310                 315                 320
Leu Arg Arg Glu Leu Asp Glu Ser Leu Gln Val Ala Glu Arg Leu Thr
                325                 330                 335
Arg Lys Tyr Asn Glu Leu Leu Lys Ser Tyr Gln Trp Lys Met Leu Asn
            340                 345                 350
Thr Ser Ser Leu Leu Glu Gln Leu Asn Glu Gln Phe Asn Trp Val Ser
        355                 360                 365
Arg Leu Ala Asn Leu Thr Gln Gly Glu Asp Gln Tyr Tyr Leu Arg Val
    370                 375                 380
Thr Thr Val Ala Ser His Thr Ser Asp Ser Asp Val Pro Ser Gly Val
385                 390                 395                 400
Thr Glu Val Val Val Lys Leu Phe Asp Ser Asp Pro Ile Thr Val Thr
                405                 410                 415
Val Pro Val Glu Val Ser Arg Lys Asn Pro Lys Phe Met Glu Thr Val
            420                 425                 430
Ala Glu Lys Ala Leu Gln Glu Tyr Arg Lys Lys His Arg Glu Glu
        435                 440                 445

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
ggcgccgaat tcatgagtcc ctggcagccc ctg                              33
```

```
<210> SEQ ID NO 3
<211> LENGTH: 41
<212> TYPE: DNA
<213> ORGANISM: Artificial Sequence
<220> FEATURE:
<223> OTHER INFORMATION: Primer

<400> SEQUENCE: 3
gggcccgtcg actcaagggc actgcaggag gtcgtaggtc a                41

<210> SEQ ID NO 4
<211> LENGTH: 37
<212> TYPE: DNA
<213> ORGANISM: Artificial Sequence
<220> FEATURE:
<223> OTHER INFORMATION: Primer

<400> SEQUENCE: 4
ggcgccgaat tccaaacctt caaaggcctc aagtggg                     37

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
gatcgaattc atgaagattc tcctgctgt                              29

<210> SEQ ID NO 6
<211> LENGTH: 63
<212> TYPE: DNA
<213> ORGANISM: Artificial Sequence
<220> FEATURE:
<223> OTHER INFORMATION: Primer

<400> SEQUENCE: 6
cgatgcggcc gctcacaggt cctcctctga gatcagcttc tgctcttccg cacggctttt    60
cct                                                          63

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
gatcgaattc atgagtccct ggcagcc                                27

<210> SEQ ID NO 8
<211> LENGTH: 59
<212> TYPE: DNA
<213> ORGANISM: Artificial Sequence
<220> FEATURE:
<223> OTHER INFORMATION: Primer

<400> SEQUENCE: 8
cgatgcggcc gctcaagcgt aatctggaac atcgtatggg taagggcact gcaggaggt     59

<210> SEQ ID NO 9
<211> LENGTH: 8
<212> TYPE: PRT
<213> ORGANISM: Artificial Sequence
<220> FEATURE:
```

```
<223> OTHER INFORMATION: Fret substrate
<220> FEATURE:
<221> NAME/KEY: MISC_FEATURE
<222> LOCATION: (1)..(1)
<223> OTHER INFORMATION: X means QLX-520-Pro, which stands for Proline
      linked to fluoresence quencher QLX520
<220> FEATURE:
<221> NAME/KEY: MISC_FEATURE
<222> LOCATION: (7)..(7)
<223> OTHER INFORMATION: X means D-arginine
<220> FEATURE:
<221> NAME/KEY: MISC_FEATURE
<222> LOCATION: (8)..(8)
<223> OTHER INFORMATION: X means Lys-(5-FAM)-NH2, which stands for
      lysine linked to 5-carboxyfluorescein, the peptide backbone is
      terminated with NH2

<400> SEQUENCE: 9

Xaa Leu Gly Leu Trp Ala Xaa Xaa
1               5

<210> SEQ ID NO 10
<211> LENGTH: 10
<212> TYPE: PRT
<213> ORGANISM: Artificial Sequence
<220> FEATURE:
<223> OTHER INFORMATION: MMP Fret substrate
<220> FEATURE:
<221> NAME/KEY: MISC_FEATURE
<222> LOCATION: (1)..(1)
<223> OTHER INFORMATION: X means QXL-520-Y-Abu which gamma-aminobutyric
      acid linked to QXL-520 fluorescence quencher
<220> FEATURE:
<221> NAME/KEY: MISC_FEATURE
<222> LOCATION: (3)..(3)
<223> OTHER INFORMATION: X means Cha which stands for Cyclohexyl methyl
      amino acid
<220> FEATURE:
<221> NAME/KEY: MISC_FEATURE
<222> LOCATION: (4)..(4)
<223> OTHER INFORMATION: X means Abu which stands for aminobutyric acid
<220> FEATURE:
<221> NAME/KEY: MISC_FEATURE
<222> LOCATION: (5)..(5)
<223> OTHER INFORMATION: X means Smc which stands for S-methyl-L-
      cysteine
<220> FEATURE:
<221> NAME/KEY: MISC_FEATURE
<222> LOCATION: (8)..(8)
<223> OTHER INFORMATION: X means Dab(5-FAM) which stands for
      diaminobutyric acid linked to 5-carboxyfluorescein
<220> FEATURE:
<221> NAME/KEY: MISC_FEATURE
<222> LOCATION: (10)..(10)
<223> OTHER INFORMATION: X means Lys-NH2, which stands for lysine with
      the backbone of the peptide terminated in NH2

<400> SEQUENCE: 10

Xaa Pro Xaa Xaa Xaa His Ala Xaa Ala Xaa
1               5                   10
```

US 10,398,755 B2

CLUSTERIN PHARMACEUTICALS AND TREATMENT METHODS USING THE SAME

CROSS REFERENCE TO RELATED APPLICATIONS

The present application is a continuation of U.S. application Ser. No. 14/473,622, which is a divisional of U.S. Non-provisional application Ser. No. 12/814,349, filed Jun. 11, 2010, which claims the benefit of the filing date of U.S. Provisional Application No. 61/186,724 filed Jun. 12, 2009, all of which are incorporated herein by reference in their entirety.

STATEMENT REGARDING FEDERALLY SPONSORED RESEARCH OR DEVELOPMENT

This invention was made with government support under Contract Nos. R01 EY12651, R01 EY09828, P30 EY14801, and P30 EY03040 awarded by the National Institutes of Health. The government has certain rights in the invention.

FIELD OF THE INVENTION

The present invention relates in general to pharmaceutical compositions comprising clusterin or polypeptides substantially the same as clusterin and to treatment methods for inflammatory diseases and dry eye disease.

BACKGROUND OF THE INVENTION

Matrix Metalloproteinases (MMPs), a family of proteolytic enzymes that participate in cell migration and matrix degradation in order to maintain and remodel the tissue structure, are zinc dependent endopeptidases. They comprise a large family of proteases that share common structural and functional elements. These enzymes are primarily distinguished from other classes of proteinases by their dependence on metal ions and neutral pH for activity. Zymogen forms of MMPs (pro-MMPs) are secreted into the matrix of a large number of cell types. (Corbel 2002) Activation of the of the pro-MMPs in the local microenvironment can subsequently result in discrete alterations in the tissue structure. The MMPs can be classified into distinct subclasses, two of which are the gelatinases (MMP-2 and MMP-9) and matrilysin (MMP-7).

There has been significant interest in MMP inhibition as a therapeutic strategy. Metal metalloproteinase inhibitors (MMPIs) have been examined as therapeutic targets for various disease states. Animal models indicate that MMPIs could be useful treatments in inflammatory diseases such as multiple sclerosis, glomerulonephritis, bacterial meningitis, uveroentinitis, graft-versus-host disease, emphysema, aortic aneurysm and restenosis after angioplasty as a treatment for atherosclerosis. (Brinckerhoff 2002) Excessive levels of MMPs are also present in various respiratory diseases. Two MMPs, MMP-2 and MMP-9 have been implicated in development of airway inflammation and pulmonary fibrosis and the modulation of MMP activity by eliminating excessive proteolytic damage has been suggested. (Corbel 2001)

Tumor necrosis factor-α, TNF-α initiates most of the essential steps of inflammation, including the increased expression of other cytokines, chemokines and proteases like MMPs. It has been demonstrated that MMP-2, MMP-9 play a role in the mouse model of TNF-induced lethal heptatitis. (See Wielockx, 2004). MMP-7 deficient mice are much less vulnerable to TNF than wild type mice, indicating MMP-7 is also important during an acute and systemic inflammation induced by TNF administration. Id. MMP 7 inhibitors have been suggested for treatment of such diseases as cancer, inflammatory lung disease, Alzheimer's disease and atherosclerosis. Id.

To date however, only one MMPI, Periostat (doxycycline hydrate) is licensed in the United States. Periostat is used to treat perodontitis. Doxycline both inhibits MMP activity and also seems to decrease MMP gene expression.

As such, there is a need for more and better agents used to treat inflammatory diseases.

Also, there is a need MMPIs capable of inhibiting or modulating MMP activity, including the activity of MMP-2, MMP-9 and MMP-7.

MMP-9 is also implicated in diseases of the eye. MMP-9 is one of the primary matrix-degrading enzymes on the corneal surface, and an increased density and activity of MMP-9 was observed in the tear fluid of dry eye patients (Afonso et al., 1999; Solomon et al., 2001). In addition to its actions on matrix proteins, MMP-9 proteolytically activates latent precursors of IL-1β and TGF-β (Schonbeck et al., 1998) and increased expression of MMP-9, IL-1b, and TNF-a have been all found in mouse corneal epithelial cells following an experimentally induced model of mouse dry eye (Solomon et al., 2001; Chen et al., 2008b). MMP-9 has also been shown to be responsible for the destruction of corneal barrier in experimental dry eye mice (Pflugfelder et al., 2005). Compared with MMP-9 deficient mice, the wild type animal suffered greater corneal epithelial permeability and desquamation of differentiated apical corneal epithelial cells (Fini et al., 1996).

The ocular surface is covered by a tear film which is composed of three layers: the outer oil layer, the middle aqueous layer, and the innermost membrane/mucin layer associated with the apical corneal epithelium. An insufficient tear supply can cause a prolonged alteration or imbalance of the tear film components on the surface. Such conditions alter the homeostasis on the ocular surface by triggering stress pathways in the epithelial cells, which can lead to "dry eye syndrome (DES)." DES causes ocular damage which is very painful and debilitating and can lead to blindness in severe cases. It affects tens of millions of people worldwide. It is accompanied by increased osmolarity of the tear film and inflammation of the ocular surface.

In DES, the stress response made by the ocular surface epithelial cells initiates an inflammatory response by activating stress signal pathways in the epithelial cells to produce various inflammatory cytokines, chemokines, and components associated with the inflammatory process (Luo et al., 2005). The combined net result of such events is the recruitment of inflammatory and immune cells to the ocular surface. The recruitment of these cells induces a feed-back loop wherein the cell secretions induce corneal epithelial cell dysfunction and damage, which in turn leads to greater inflammation and leads to disease progression (Pflugfelder et al., 2008). Dry eye patients have increased levels of various inflammatory mediators in their tear fluid such as interleukin IL-6, IL-8, and TNF-alpha, and IL-12.

To date, however, treatments for dry eye disease have been inadequate.

Clusterin (CLU), also known as apolipoprotein J, testosterone-repressed prostate message-2, or sulphate glycoprotein-2, is a secreted disulfide-linked heterodimeric glycoprotein (70-80 KD) that plays a role in multiple biological events including apoptosis, oxidative stress, sperm maturation, complement regulation, and cytoprotection (Shannan et al., 2006). Initially, CLU was thought to be a marker of cell death because its levels of expression increase in various lesions undergoing cell death. Recent studies have suggested that it also has a role in protecting cells from cell death, and has now become a target for certain cancer therapies (Chung et al., 2004). Following infection, the CLU levels increase as both a positive acute and chronic phase response protein in patients (Chen et al., 2008a) and animal models (Sharma et al., 2008).

SUMMARY OF THE INVENTION

One aspect of the present invention is the identity of novel protein and polypeptide binding partners for MMP-2, MMP-7 and MMP-9 or the pro-MMP analogues.

Another aspect of the present invention is the discovery that clusterin and polypeptides substantially the same as clusterin interact with and inhibit MMP-2, MMP-7 and MMP-9.

Another aspect of the present invention is the discovery that the interaction and inhibition does not require the processing or modification of either clusterin or the MMPs. The significance of their interaction was demonstrated by the observation that CLU inhibited the enzymatic activity of MMP-9.

It is another aspect of the present invention that clusterin can be rendered MMP-2 and MMP-9 soluble in a non-ionic detergent condition.

Another aspect of the present invention is direct to a pharmaceutical composition comprising an isolated clusterin or an isolated polypeptide substantially the same as clusterin. Preferably, the clusterin is secreted clusterin. Preferably, the pharmaceutical composition comprises a carrier, and even more preferably the carrier is a sterile solution.

Another aspect of the present invention is a method of treating dry eye disease comprising administering to a patient in need thereof an effective amount of a pharmaceutical composition comprising an isolated clusterin or an isolated polypeptide substantially the same as clusterin. Preferably, the pharmaceutical composition comprises secreted clusterin. Preferably, the pharmaceutical composition is administered topically. Even more preferably, the pharmaceutical composition further comprises a liquid carrier, and administration is by contacting the pharmaceutical composition to the surface of an eye of the patient.

Another aspect of the present invention is directed to a method of treating a disease state characterized by inflammation comprising administering to a patient having the disease state an amount of isolated clusterin or a protein substantially the same as clusterin effective to decrease the activity of a matrix metallproteinase selected from the group consisting of MMP-9, MMP-2 and MMP-7. The disease state treated may include inflammatory lung disease, cancer, multiple sclerosis, Alzheimer's disease, artherosclerosis, airway inflammation, pulmonary fibrosis, glomerulonephritis, bacterial meningitis, uveroentinitis, graft-versus-host disease, emphysema, aortic aneurysm and restenosis after angioplasty as a treatment for atherosclerosis.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

The arrow head indicates a DNA marker of 400 bp. (B) Western blot of the media from the HOLE cell culture with anti-CLU antibody sc-6419. Lane 1 contains conditioned medium (K-sfm) from the cell culture; lane 2 has regular medium (K-sfm plus BPE and EGF) from the culture; and lane 3 includes fresh regular medium as a control. The arrow indicates the position of the β-subunit of CLU with the expected size of ~40 KD.

Figure 9:
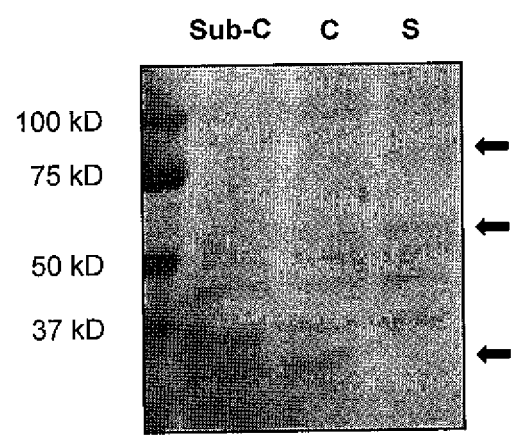

FIG. 9 shows that intracellular processing of CLU is affected by growth conditions. Western blot using anti-CLU antibody of HCLE cells grown at the subconfluent cell density (Sub-C), confluent cell density (C), or stratified corneal cells (S). The arrows indicate CLU bands that increased or decreased in the stratified cells, as compared to the other two.

Figure 10:
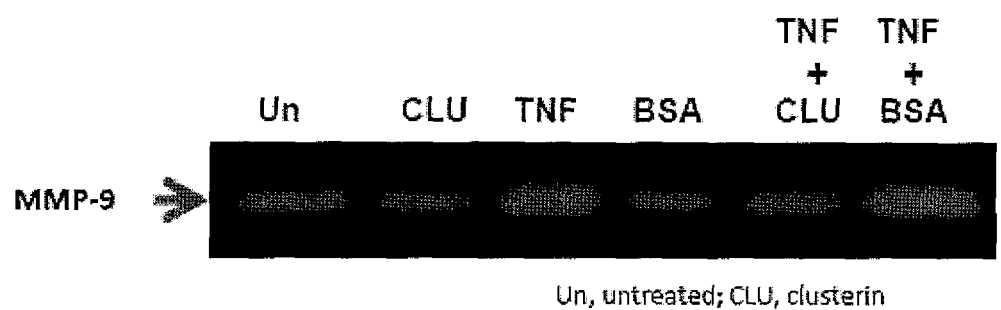

FIG. 10 shows that Clusterin inhibits the induction of MMP-9 by TNF-alpha from human corneal limbal epithelial (HCLE) cells. HCLE cells were grown to be confluent in KSFM media and then replenished with DMAM/F12 media to stratify cells for 7 days. To these cells in serum-free DMEM/F12 media, clusterin (50 ug/ml), bovine serum albumin (BSA, 50 ug/ml), and TNF-alpha (10 ng/ml), individually or in combination, were treated for 24 hours. The same volume of supernatants of the cell cultures treated were collected to resolve on SDS/PAGE gel containing gelatin in order to perform gelatin zymography to visualize the presence of MMP-9 secreted from the cells.

DETAILED DESCRIPTION OF THE INVENTION

Abbreviations
MMP, matrix metalloproteinase;
CLU, clusterin;
TIMP, tissue inhibitor of matrix metalloproteinase;
BSA, bovine serum albumin;
APMA, 4-aminophenylmercuric acetate;
SB-3CT, 3-(4-phenoxyphenylsulfonyl)-propylthiirane;
FRET, fluorescence resonance energy transfer
Definitions Unless otherwise indicated, all terms used herein have the meanings given below, and are generally consistent with same meaning that the terms have to those skilled in the art of the present invention. It is to be understood that this invention is not limited to the particular methodology, protocols, and reagents described, as these may vary.

The term "clusterin" refers to human clusterin, including secreted clusterin and nuclear clusterin, or any subunit, fragment or region of either capable of binding to, or reducing the activities of MMP-9, MMP-2 or MMP-7. The term clusterin optionally encompasses non-peptidic components, such as carbohydrate groups or any other non-peptidic substituents that may be added to clusterin by a cell in which the protein is produced, and may vary with the type of cell.

The terms "treatment" or "treating" refers to both therapeutic treatment and prophylactic or preventative measures, wherein the object is to prevent or slow down (lessen) the targeted pathologic condition or disorder. It may also encompass relief of symptoms associated with a pathological condition or disorder. Those in need of treatment include those already with the disorder as well as those prone to have the disorder or those in whom the disorder is to be prevented.

An "effective amount" of isolated clusterin or an isolated polypeptide substantially the same as clusterin is an amount sufficient to decrease the activity or the amount of a target matrix metalloproteinase. An "effective amount" may be determined empirically and in a routine manners in relation to the stated purpose.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS9™.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "substantially the same" refers to nucleic acid or amino acid sequences having sequence variation that do not materially affect the ability of the amino acid sequence to bind to or reduce the activity of the target metalloproteinase, e.g. MMP-9, MMP-7, MMP-2. With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

As used herein, the term "expression" or "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively. A protein is "inappropriately expressed" if it is expressed in different places, at different times, or in different amounts in an organism characterized by a disease state than it is in an organism with no disease.

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

Pharmaceutical Compositions

One aspect of the present invention is directed to a pharmaceutical composition comprising an isolated clusterin or an isolated polypeptide substantially the same as clusterin. Preferably, the clusterin is secreted clusterin. Preferably, the pharmaceutical composition comprises a carrier, and even more preferably the carrier is a sterile solution.

Human clusterin (CLU) is composed of two disulfide-linked α (34-36 kD) and β (36-39 kD) subunits derived from a single amino acid chain (449 amino acids in human) that becomes glycosylated in the endoplasmic reticulum and Golgi bodies and undergoes intramolecular cleavage and dimerization before secretion. The first 22 amino acids comprise the secretory signal sequence. The cleavage site between the α and β chains is between amino acids 227 and 228. Clusterin contains three hydrophobic domains, a long α-helix motif near the amino terminal and at least six N-linked glycosylation sites. Clusterin also contains a hemopexin-like domain at the C-terminus of the enzyme, which modulates the processing and activity of the enzymes by serving as a binding region for regulatory or target proteins The sequence listing of Clusterin Isoform 2 Preproprotein [*Homo sapiens*] (SEQ ID NO: 1) (NCBI Reference Sequence: NP_976084.1) is as follows:

Origin

```
  1   mmktlllfvg  llltwesgqv  lgdqtvsdne  lqemsnqgsk  yvnkeiqnav  ngvkqiktli
 61   ektneerktl  lsnleeakkk  kedalnetre  setklkelpg  vcnetmmalw  eeckpclkqt
121   cmkfyarvcr  sgsglvgrql  eeflnqsspf  yfwmngdrid  sllendrqqt  hmldvmqdhf
181   srassiidel  fqdrfftrep  qdtyhylpfs  lphrrphfff  pksrivrslm  pfspyeplnf
241   hamfqpflem  iheaqqamdi  hfhspafqhp  ptefiregdd  drtvcreirh  nstgclrmkd
301   qcdkcreils  vdcstnnpsq  aklrreldes  lqvaerltrk  ynellksyqw  kmlntsslle
361   qlneqfnwvs  rlanitqged  qyylrvttva  shtsdsdvps  gvtevvvklf  dsdpitvtvp
421   vevsrknpkf  metvaekalq  eyrkkhree
```

In vivo, the human precursor polypeptide chain is cleaved proteolytically to remove the 22 amino acid secretory signal peptide and subsequently between residues 227/228 to generate the alpha and beta chains. These are assembled in an anti-parallel fashion to give a heterodimeric molecule in which the cysteine-rich centers are linked by five disulfide bridges and are flanked by two predicted coiled-coil alpha-helices and three predicted amphipathic alpha-helices.

The clusterin of the present invention can be human clusterin, including secreted clusterin and/or nuclear clusterin, or any subunit, fragment or region of either capable of binding to, or reducing the activities of MMP-9, MMP-2 or MMP-7. The subunits, fragments or regions may be tested for ability to bind or reduce the activities of MMP-9-MMP2 or MMP-7 as described in the accompanying Examples. Acceptable subunits may include human or secreted clusterin without the secretary signal sequence and/or without the hemopexin-like domain at the C-terminus of the enzyme. The term clusterin also encompasses polypeptides with optional non-peptidic components, such as carbohydrate groups or any other non-peptidic substituents that may be added to clusterin by a cell in which the protein is produced, and may vary with the type of cell.

Recombinant human clusterin may be purchased from any number of known sources, expressed in cell lines of mouse and human. It may also be isolated from human serum by known methods. Any subunit, fragment or region may be isolated or synthesized according to known techniques for polypeptide synthesis.

The pharmaceutical compositions of the present invention may also include polypeptides substantially the same as human clusterin, secreted clusterin, nuclear clusterin or any subunit, fragment or region of either capable of binding to, or reducing the activities of MMP-9, MMP-2 or MMP-7. Generally, amino acid sequences are substantially the same if they have a sequence variation that do not materially affect the ability of the protein, subunit, fragment or region bind to or reduce the activity of MMP-9, MMP-2 or MMP-7. These polypeptides can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art. The subunits, fragments or regions may be tested for ability to bind or reduce the activities of MMP-9-MMP2 or MMP-7 as described in the accompanying Examples. The polypeptides of the present invention may be made by known techniques for polypeptide synthesis.

The polypeptides of the present invention which occur naturally, or are synthesized according to known methods, are generally "isolated." Specifically, the should be used in the pharmaceutical composition of the present invention in a condition other than their respective native environment, such as apart from blood and animal tissue. In a preferred embodiment, the isolated polypeptide is substantially free of other polypeptides, particularly other polypeptides of animal origin. It is preferred to provide the polypeptides in a highly purified form, i.e. greater than 95% pure, more preferably greater than 99% pure.

The pharmaceutical compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Compositions and formulations for oral administration include powders or granules, suspensions or solutions in water or non-aqueous media, capsules, sachets or tablets. Thickeners, flavoring agents, diluents, emulsifiers, dispersing aids or binders can be desirable.

Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, and drops. The compositions of the present invention can also be formulated as suspensions in aqueous, non-aqueous or mixed media. Aqueous suspensions can further contain substances that increase the viscosity of the suspension including, for example, sodium carboxymethylcellulose, sorbitol and/or dextran. The suspension can also contain stabilizers.

The compositions of the present invention can additionally contain other adjunct components conventionally found in pharmaceutical compositions. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

Dosing is also dependent on severity and responsiveness of the disease state to be treated, with the course of treatment lasting from several days to several months, or until symptomatic relief or a cure is effected or a diminution of the disease state is achieved. The administering physician can determine optimum dosages, dosing methodologies and repetition rates. Optimum dosages can vary depending on the relative potency of individual polypeptide and should generally be sufficient to reduce the activity of the target MMP, either MPP-2, MMP-9 or MMP-7. Following successful treatment, it can be desirable to have the subject undergo maintenance therapy to prevent the recurrence of the disease state, wherein the polypeptide is administered in maintenance doses.

An especially preferred dosage form is a sterile solution for topical use, such as use as drops. Therapeutic formulations are prepared for storage by mixing the active ingredient having the desired degree of purity with optional physiologically acceptable liquid carrier, and optionally other excipients or stabilizers (Remington's Pharmaceutical Sciences 16th edition, Osol, A. Ed. (1980)), to produce an aqueous solution or suspension. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, ordextrins; chelating agents such as EDTA; sugar alcohols such as mannitol or sorbitol.

The solution or suspension formulations should be sterile. This is readily accomplished by filtration through sterile filtration membranes, prior to or following lyophilization and reconstitution. The resulting therapeutic compositions herein generally are placed into a container and the route of administration is in accord with known methods, e.g. injection or infusion by intravenous, intraperitoneal, intracerebral, intramuscular, intraocular, intraarterial or intralesional routes, topical administration, or by sustained release systems.

Treatment Methods for Dry Eye Disease

Another aspect of the present invention is a method of treating dry eye disease comprising administering to a patient in need thereof an effective amount of a pharmaceutical composition comprising an isolated clusterin or an isolated polypeptide substantially the same as clusterin.

It should be understood that the terms "treatment" or "treating" refers to both therapeutic treatment and prophylactic or preventative measures, wherein the object is to prevent or slow down (lessen) the targeted pathologic condition or disorder. Treatment should also be understood to include relief of the symptoms of the disease. Those in need of treatment include those already with the disorder as well as those prone to have the disorder or those in whom the disorder is to be prevented.

An "effective amount" of isolated clusterin or an isolated polypeptide substantially the same as clusterin is an amount sufficient to decrease the activity or the amount of a target matrix metalloproteinase. In the case of dry eye disease, the target metalloproteinase is preferably MMP-9. Generally, not all the activity target metalloproteinase need be eliminated. Rather, the activity of the target metalloproteinaise need only be reduced by an amount sufficient to reach the therapeutic goal. For instance, if the goal of the treatment is preventative, the amount of the reduction of activity need only be sufficient to prevent dry eye disease. Thus, an effective amount may be determined empirically and in a routine manner in relation to the stated purpose.

The clusterin used in the connection with the method may be any isolated clustering or a polypeptide substantially the same as clusterin that can reduce the activity of the target metalloproteinase in the eye. Most preferably, the pharmaceutical composition comprises secreted clusterin.

In accordance with the present invention, clusterin can inhibit the activity of MMP-9 extracellularly in epithelial cells. As such, the pharmaceutical composition for use in the treatment of dry eye disease is administered topically. Preferably, when topically administered, the clusterin is combined with a liquid carrier, and administration in the form of an eye drop by contacting the pharmaceutical composition to the surface of an eye of the patient. The concentration of the clusterin in the resulting liquid pharmaceutical should be sufficiently high that when administered to the patient, there is a sufficient concentration of clusterin to reduce the activity sufficient to produce the required result.

Treatment Method for Inflammatory Diseases

Another aspect of the present invention is directed to a method of treating a disease state characterized by inflammation comprising administering to a patient having the disease state an amount of isolated clusterin or a protein substantially the same as clusterin effective to decrease the activity of a matrix metallproteinase selected from the group consisting of MMP-9, MMP-2 and MMP-7. The disease state treated may include inflammatory lung disease, cancer, multiple sclerosis, Alzheimer's disease, artherosclerosis, airway inflammation, pulmonary fibrosis, glomerulonephritis, bacterial meningitis, uveroentinitis, graft-versus-host disease, emphysema, aortic aneurysm and restenosis after angioplasty as a treatment for atherosclerosis.

It should be understood that the terms "treatment" or "treating" refers to both therapeutic treatment and prophylactic or preventative measures, wherein the object is to prevent or slow down (lessen) the targeted pathologic condition or disorder. Treatment should also be understood to include relief of the symptoms of the disease: Those in need of treatment include those already with the disorder as well as those prone to have the disorder or those in whom the disorder is to be prevented.

An "effective amount" of isolated clusterin or an isolated polypeptide substantially the same as clusterin is an amount sufficient to decrease the activity or the amount of a target matrix metalloproteinase. The identity of target metalloproteinase, either MMP-9, MMP-7 or MMP-2, will generally depend on the disease state to be treated. Generally, not all the activity target metalloproteinase need be eliminated. Rather, the activity of the target metalloproteinaise need only be reduced by an amount sufficient to reach the therapeutic goal. In addition, since normal functioning of tissue associated with the inflammation may require some level of target metalloproteinase activity, the activity of the target metalloproteinase should not be reduced below a level needed for adequate functioning of the target tissue. Thus, an effective amount may be determined empirically and in a routine manner in relation to the stated purpose. For instance, if the goal of the treatment is preventative, the amount of the reduction of activity need only be sufficient to prevent dry eye disease.

The clusterin used in the connection with, the method may be any isolated clusterin or a polypeptide substantially the same as clusterin that can reduce the activity of the target metalloproteinase in the tissue affected by the disease state.

Administration can be administered in a number of ways depending upon whether local or systemic treatment is desired and upon the area to be treated.

EXAMPLES

The following examples are provided in order to demonstrate and further illustrate certain embodiments and aspects of the present invention and are not to be construed as limiting the scope thereof. While such examples are typical of those that might be used, other procedures known to those skilled in the art may alternatively be utilized. Indeed, those of ordinary skill in the art can readily envision and produce further embodiments, based on the teachings herein, without undue experimentation.

Materials and Methods

Cells—

Cells of the human embryonic kidney cell line, HEK293 were grown in DMEM containing 10% FBS, 100 units/ml penicillin, and 100 µg/ml streptomycin in a cell culture incubator at 37° C., 5% $CO_2$. Immortalized human corneal-limbal epithelial (HCLE) cells, kindly provided by Dr. Ilene Gipson (Harvard University) were grown in Gibco keratinocyte SFM media (Gibco BRL, Carlsbad, Calif.) [Argueso, 2006].

MMP-9 cDNA Constructs—The entire MMP-9 cDNA (coding amino acid 1-703) was reverse transcribed and amplified from mouse muscle tissue. Primers MMP9.1
(SEQ ID NO: 2)
(5'-GGCGCCGAATTCATGAGTCCCTGGCAGCCCCTG-3')
and

MMP9.2109
(SEQ ID NO: 3)
(5'-GGGCCCGTCGACTCAAGGGCACTGCAGGAGGTCGTAGGTCA-3')

incorporating EcoR I and Sal I sites, respectively, was used. This rt-PCR product was inserted into the yeast expression vector pGBKT7 and labeled pGB-M9. Utilizing the pGB-M9 plasmid as a template an N-terminus MMP-9 truncated PCR product missing the signal and propeptide domain (amino acid 109-703) was generated using primers

MMP-9.325
(SEQ ID NO: 4)
(5'-GGCGCCGAATTCCAAACCTTCAAAGGCCTCAAGTGGG-3')

MMP9.2109 primers and labeled pGB-M9ΔPP. The GST tagged MMP-9 constructs were generated by ligation of the pGB-M9 and pGB-M9ΔPP EcoR I/Sal I inserts into the pGEX 4T vector (Amersham, Piscataway, N.J.).

Library Construction and Screening—

Whole mouse cornea was excised and total RNA isolated via the TRIzol reageant (Invitrogen, Carlsbad, Calif.). The cDNA library was synthesized using 2 µg total RNA and random primers per the protocol for the Matchmaker Two-Hybrid System (Clontech, Mountain View, Calif.). This yeast two hybrid system utilizes an in vivo library construction method; therefore the cDNA library and the linearized yeast expression vector pADT7-Rec were simultaneously transfected into the AH109 pGB-M9ΔPP stable yeast cells. Positive colonies were selected on quadruple knock-out plates, yeast minimal agar plates lacking tryptophan, leucine, histidine and adenine. The two reporter genes testing for interactions are the histidine and adenine. An additional screen involved the addition of X-α-galactosidase to the quadruple knocked-out media, whereby a positive interaction allowed for blue/white screening.

Yeast Plasmid Isolation—

Positive colonies were inoculated into an overnight culture of YAPD media and plasmid isolation performed upon saturation using the following yeast lysis method. Briefly, pelleted yeast cells were vortexed in equal volume yeast lysis buffer (2% Triton X-100, 1% SDS, 0.1 M NaCl, 10 mM Tris-HCl (pH 8.0), 1 mM EDTA) and phenol-chloroform-isoamyl alcohol [25:24:1] with acid washed glass beads. The clarified supernatant was ethanol precipitated in the presence of NaOAc. The resulting DNA complex was transformed into XL1-blue bacterial cells and colonies selected on ampicillin plates to select for the pADT7-library clone. The resulting bacterial colonies were lysed via the standard alkaline lysis protocol and the plasmids sequenced.

Sequence Analysis—

The DNA sequence were translated based on the reading frame given for the pADT7-Rec vector and both the protein sequence and DNA sequence subjected to BLAST searches in GENBANK. The DNA sequence were translated into protein sequence using the translate tool at the ExPASy Bioinformatics Resource Portal website. Dual searches were done to confirm that the protein sequence translated matched their DNA sequences, mismatching clones were discarded.

GST Pull-Down Assays—

The GST tagged MMP-9 constructs were generated by ligation of the pGB-MMP-9 EcoR I/Sal I inserts into the pGEX 4T vector (Amersham, Piscataway, N.J.). The pGEX 4T MMP-9 constructs were transformed into the E. Coli strain BL21(DE3) (Novagen, Gibbstown, N.J.) for expression. The bacterial pellet was prepared from a 100 ml culture that was grown to mid-log phase, induced with 0.4 mM isopropyl β-D-thiogalactopyranoside for three hours, followed by centrifugation. The pellet was resuspended and lysed by sonication in ST buffer (50 mM Tris pH 7.4, 100 mM NaCl, 1 µg/ml leupeptin, 1 µg/ml aprotinin, 1 mM PMSF, 1 mM NaF), and GST-MMP-9 protein purified via incubation with glutathione coated beads (Amersham, Piscataway, N.J.) overnight at 4° C. The next day the beads were extensively washed in ST buffer. To confirm production of GST-MMP-9 protein, the beads were electrophoresed on an 8% SDS-PAGE gel. The gel was subjected to Coomassie Brilliant Blue Staining or transferred to PVDF membrane and immunoblotted using a rabbit polyclonal antibody to MMP-9 (Triple Points Biologics, Inc.). Using the TNT quick coupled transcription/translation system (Promega, Madison, Wis.) the pADT7-CLU clone generated an HA tagged CLU fusion protein. The GST-MMP-9 or GST coated beads were incubated with equal amounts of HA-CLU overnight at 4.0 in immunoprecipitation (IP) buffer (50 mM Tris, pH 7.4, 100 mM NaCl, 0.1% Triton X-100, 1 µg/ml leupeptin, 1 µg/ml aprotinin, 1 mM PMSF, 1 mM NaF) in the presence or absence of 1 mg/ml BL21 bacterial soluble extract (to decrease non-specific background). The following day the beads were washed 3 times in IP buffer, resuspended in SDS-PAGE loading buffer, electrophoresed on an 8% SDS-PAGE gel, transferred and immunoblott using a mouse HA antibody (Santa Cruz, Calif.).

Generation of Expression Vectors for MMP-9 and CLU—

The pcDNA3.1(+) expression vector (Invitrogen, Carlsbad, Calif.) was used to insert PCR fragment generated using pGB-M9 as a template with the gene-specific primers containing EcoR I (in forward primers) or Not I (in reverse primers) sites: Mouse CLU with C-terminal a Myc tag (CLU-Myc), (SEQ ID NO: 5)
5-GATCGAATTCATGAAGATTCTCCTGCTGT
and (SEQ ID NO: 6)
5'-CGATGCGGCCGCTCACAGGTCCTCCTCTGAGATCAGCTTCTGCTCTT

CCGCACGGCTTTTCCT;

and mouse MMP-9 with a C-terminal HA tag (MMP-9-HA), (SEQ ID NO: 7)
5'-GATCGAATTCATGAGTCCCTGGCAGCC
and (SEQ ID NO: 8)
5'-CGATGCGGCCGCTCAAGCGTAATCTGGAACATCGTATGGGTAAGGGC

ACTGCAGGAGGT.

The DNA sequence of cloned DNA was confirmed by DNA sequencing.

Immunoprecipitation Assay—

HEK293 cells were grown in subconfluent culture in 6-well plate, and transfected with 2.5 µg of pcDNA3.1 (+)/MMP-9, pcDNA3.1 (+)/MMP CLU, or both, using Lipofectamine LTX according to the manufacturer's instruction (Invitrogen Inc., Carlsbad, Calif.). One day post transfection, whole cell extracts were prepared using RIPA buffer, incubated with anti-HA antibody to immunoprecipitate HA tagged MMP-9 and partners. The complexes were resolved on a denaturing SDS/PAGE gel for immunoblotting to detect Myc tagged CLU proteins with anti-Myc antibody.

Confocal Microscopy—

HCLE (5000 cells/well) were plated into 16-well chamber slide. The cells were allowed to adhere and proliferate for 48 hours before immunocytochemical analysis. The cells were washed once with PBS and then fixed in ice cold methanol for 10 minutes. Next, the cells were washed three times with PBS followed by blocking with 1% BSA and 0.25% Triton-X 100 in PBS for one hour at room temperature. The cells were then incubated at room temperature for 45 minutes with both goat anti-CLU (1:50) and rabbit anti-MMP-9 (1:50) antibodies in the blocking solution. Following the primary antibody incubation, cells were washed three times with PBS for 5 minutes each then incubated at room temperature for one hour with both donkey anti-goat-FITC (1:2000) and goat anti-rabbit-Rhodamine (1:2000) secondary antibodies. Subsequently, the cells were washed three times with PBS for five minutes each and rinsed once with distilled water. The cells were then covered with a drop of vectastain (containing DAPI) and coverslipped. Cells were imaged on a Perkin Elmer Ultraview ERS Spinning Disk Laser Confocal Microscope at a total magnification of 400 times.

MMP Inhibition Assay—

MMPs were mixed with CLD in TSCB buffer, 50 mM Tris-HCl, pH, 7.5, 150 mM NaCl, 5 mM $CaCl_2$, 0.002% Brij35 (or otherwise indicated concentration) 30 min prior to substrate addition, and incubated for 3 h at RT in the presence or absence of 0.02 mM p-aminophenylmercuric acetate (APMA). MMP activity was measured using a 5-FAM/QXL520 fluorescence resonance energy transfer (FRET) peptide as a substrate (EX1Em=490 nm/520 nm) (AnaSpec, Fremont, Calif.), according to the manufacturer's protocol. Relative fluorescence unit (RFU) was obtained by subtracting the values of APMA- or enzyme-omitted reactions from those of test samples, and then considering the fluorescence unit of a PBS (vehicle) sample as 100%. Enzyme reactions were performed in black 96-well plate, containing combinations of 10 ng, 5 ng, 5 ng, 10 ng, 2.5 µg, 2.5 µg of MMP-2, MMP-7, catalytic domain of MMP-9, MMP-9, CCLU, and/or BSA, respectively, in 50 µl reaction volume. As MMP substrates (0.4 µM), 520 MMP FRET substrate I, QLX520-Pro-Leu-Gly-Leu-Trp-Ala-D-Arg-Lys (5-FAM)-$NH_2$ (SEQ ID NO: 9), was used for MMP-2 and MMP-9, and 520 MMP FRET substrate XIV, QXL520-γ-Abu-Pro-Cha-Abu-Smc-His-Ala-Dab(5-FAM)-Ala-Lys-$NH_2$ (SEQ ID NO: 10), used for MMP-7 reactions, both of which were purchased from AnaSpec (Fremont, Calif.). Recombinant proteins such as mouse CLU with C-terminal $(His)_6$ (CLU-His), MMP-2, and MMP-7 were purchased from R&D Systems (Minneapolis, Minn.), MMP-9 was purchase from Ana-Spec, Inc. (San Jose, Calif.). The recombinant catalytic domain of human MMP-9 (residue 112-445) was purchased from ProtEra (Sesto Fiorentino, Italy). A gelatinase-specific synthetic inhibitor, SB-3CT, was obtained from Biomol International (Plymouth Meeting, Pa.). Fluorescence was monitored using a Victor³™ V multilabel counter (PerkinElmer). For the gelatin digestion, a 50 µl mixture of gelatin (20 µg) and CLU (2 µg) was incubated with or without active MMP-9 (70 ng) for 2 hours at 37° C. The reaction products were run on a 12% denaturing SDS/PAGE gel for Coomasie staining.

Gelatin Zymography—

Zymographic analysis was used to analyze the relative amounts of MMPs and was performed according to the procedure described by [Gordon, 2009]. Briefly, Samples were loaded into an 8% PAGE gel containing 0.1% gelatin (Sigma-Aldrich). Gels were run for 45 min at 200 V. Gels were then incubated in 2.5% Triton-X for 1 h at RT on a rocker. Gels were thoroughly washed with distilled water and incubated overnight in renaturing buffer (10 mM $CaCl_2$, 50 mM Tris-HCl pH 7.5) at 37° C. The next morning, gels were briefly washed and then stained (25 g Coomassie blue, 150 ml isopropanol, 50 ml acetic acid, 300 ml H2O) for 1 h at RT on a rocker. Gels were then de-stained in distilled water until bands were clearly visible. Gels were then scanned for densitometric analysis.

Gelatinase Precipitation Assay— pro-MMP-2 or -9 (5 ng/tube) were incubated in TSCB buffer containing 0.05% non-ionic detergents indicated in the presence of CLU (1.25 µg/tube) or PBS (vehicle control) at RT for 80 min, followed by microcentrifugation for 2 min at 15K RPM to separate the soluble and insoluble fractions, which were resolved in zymography. Densities of the bands were quantified using Image J analysis. Relative solubility was calculated by dividing the density of soluble band with the combined densities of soluble and insoluble bands in each set of reactions.

In Vitro Protein Binding Assay—

To make various processed forms of MMPs, pro-MMPs were incubated with 1 mM APMA in TSCB buffer at 37° C. for 4 h to make C-terminal truncated processed MMP-9 (MMP-9-ΔC) [Murphy, 1995]. CLU-His (2.5 µg) was incubated with mixture of 30-100 ng of pro-MMP-9, MMP-9, and MMP-9-ΔC, in the TSCB buffer with 0.002 or 0.04% Brij 35 for 1 h at 4° C. followed by additional incubation for 1.5 h with anti-His tag antibody-conjugated agarose beads. The beads were washed three times with the binding buffer, and dissolved in 1×SDS sample loading buffer. Relative amounts of bound MMPs were assessed on the gelatin zymography. In order to perform CLU binding domain analysis, pro-MMP-9 bound to CLU-coupled beads was prepared, as described above, and then divided into two aliquots. They were incubated with and without 1 mM APMA at RT for 1 h in TSCB buffer on the rotator. The beads (B) were spun down and solution (S) was separated. The beads were washed with TSCB and resuspended in SDS sample loading buffer. Equivalent volume of S and B fraction were subjected to gelatin zymography.

Example 1

Interaction of CLU with MMP-9

Figure 2:
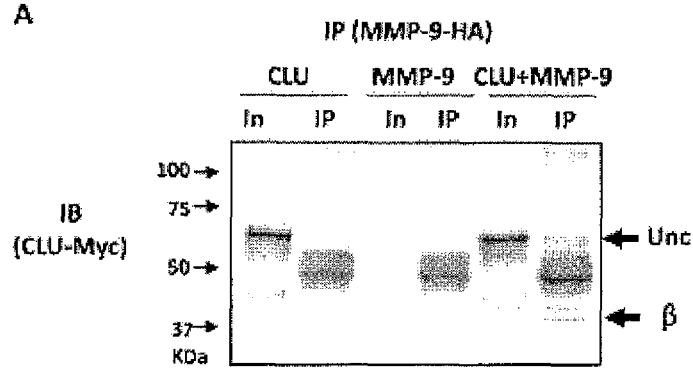
FIG. 2 shows MMP-9 binds to CLU in the cytoplasm of human cells. (A) pcDNA 3.1 (+) expression vectors carrying the mouse full length cDNA of Myc-tagged CLU (CLU) or HA-tagged MMP-9 (MMP-9) were transfected, alone (CLU or MMP-9) or combined (CLU+MMP-9), into HEK293 cells. Using the whole cell lysates of the transfected cells, immunoprecipitation (IP) with anti-HA antibody was performed to pull down MMP-9, and then the eluted samples were subjected to immunoblotting (denaturing 4-15% gradient SDS/PAGE gel) (IB) using anti-Myc antibody to detect CLU. The bands indicated by arrows are consistent to the forms of CLU undergoing intracellular processing. in, whole cell lysate used as input; IP, immunoprecipitated sample; Unc, Uncleaved CLU protein; β, β subunit of CLU. (B) Confocal microscopy of MMP-9 and CLU in HCLE cells. Nuclei were stained with DAPI, MMP-9 was detected by rhodamine-conjugated antibody, and CLU by FITC-conjugated antibody. In control, primary antibodies were omitted. The images were taken at 400× magnification.
Figure 2:
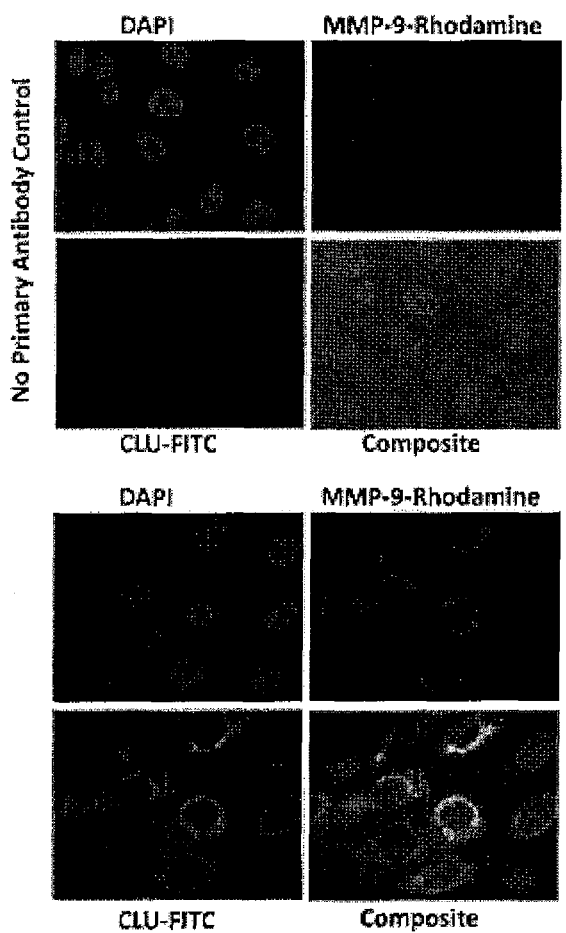

Previous results indicate that CLU protein can bind to MMP-9 without undergoing post-translational processing of the protein. To examine the possibility that they can form a complex inside the cells, we constructed two expression vectors carrying mouse cDNA of Myc-tagged CLU or HA-tagged MMP-9 protein. We transfected HEK293 cells with the two vectors, alone or combined, and then performed the immunoprecipitation (IP) assay using the whole cell lysates of the transfected cells to pull down MMP-9, and then used Western blotting to detect any CLU protein pulled down together with MMP-9 (FIG. 2A).

The bands indicated by arrows (FIG. 2A) are consistent with the forms of CLU undergoing intracellular processing (Burkey et al., 1991). Multiple CLU bands were detected in the IP sample using the cotransfected cell lysate that were not detected in the IP from CLU transfection alone, indicating that they form a complex with MMP-9 inside the cells. These results suggest the possibility that MMP-9 keeps CLU inside the cells by interacting with those proteins during processing. As such, CLU intermediates were not detected without MMP-9 coexpression (de Silva et al., 1990; Burkey et al., 1991). This may support and explain a previous report that shows that processing and secretion takes place very quickly, with a half-time of 30-35 min (Burkey et al., 1991).

Next, we tested the interaction of secreted CLU using mouse recombinant proteins. We used purified recombinant proteins of MMP-2, MMP-9, and CLU that were secreted from a mouse myeloma cell line (NSO). All of the proteins were purchased from R&D Systems. A mixture of MMP-2, MMP-9, and C-terminal truncated MMP-9 (9-ΔC) was incubated with His-tagged CLU, and subjected to the pull-down assay, using 150 mM NaCl-containing binding buffer and anti-His tag antibody resins. Portions of the input samples (Input) and proteins bound to the antibody (Bound) were resolved on the gelatin zymography gel.

Figure 7:
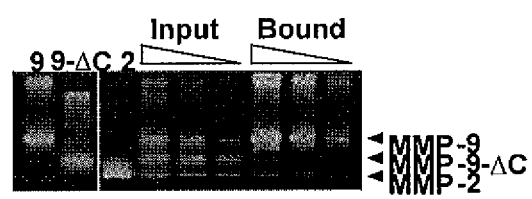
FIG. 7 shows that CLU binds to MMP-2 and MMP-9. A mixture of MMP-2, MMP-9, and C-terminal truncated MMP-9 (9-ΔC) was incubated with His-tagged CLU, used in a pull-down assay and resolved on a gelatin zymography gel. The input and bound samples were loaded in a series of dilution.

The recombinant CLU contains a $(His)_6$-Tag at the C-terminus of the protein, which was used for pull-down experiments with anti-His tag antibody beads. It was previously reported that CLU also binds to MT6-MMP/mmp-25 and that the hemopexin domain in the MMP C-terminal region is required for their interaction (Matsuda et al., 2003). To use as an internal control for the binding experiment, we removed part of MMP-9 (MMP-9-ΔC) by promoting self-processing by APMA (4-aminophenylmercuric acetate) treatment. For the in vitro binding assay we mixed MMP-2, MMP-9, and MMP-9-ΔC (FIG. 7).

Figure 8:
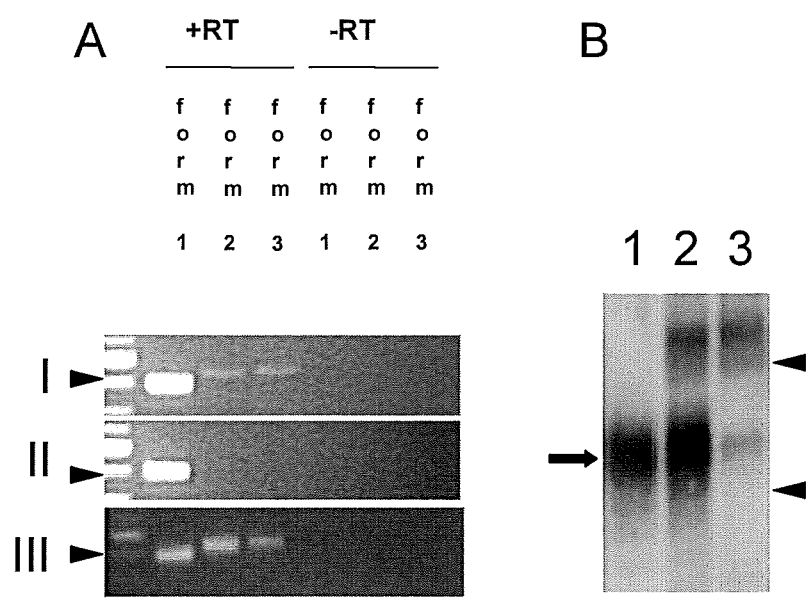
FIG. 8 shows that CLU is expressed and secreted from corneal epithelial cells. (A) Gel of isoforms 1, 2, and 3 of total RNA purified from HCLE cells (I), human corneal epithelial tissue (II), and human periodontal ligament stem cells (III). A reverse transcriptase minus (−RT) sample was used as a control.

The initial MMP-9 protein shows a high molecular weight smear above MMP-9, which are presumably aggregates of MMP-9, since we did not detect them in the heat treated reducing condition used for Western blotting (FIG. 8). The input and bound samples were loaded in a series of dilution so that the relative densities of the bands could be easily assessed.

After comparing the relative densities of protein bands in the same lane for the input and the bound, we found that MMP-9 was highly enriched in the bound sample. Though weaker than MMP-9, MMP-2 also had an affinity for CLU while the truncated MMP-9 did not. We conclude that MMP-2 and MMP-9 interact with CLU.

Example 2

CLU and MMP-9 Interact Inside and Outside of Cells

To identify corneal proteins, including CLU, that interact with MMP-9, the yeast two hybrid system was employed. We used mouse MMP-9 cDNA corresponding to active MMP-9 lacking the N-terminal signal peptide and propeptide domains. Recovery of the colonies supported on the knock out media and expressing galactosidase activity identified 24 potential prey sequences. Sequence analysis of the rescued pADT7 plasmids found many candidates known to be present in extracellular region or in cell membrane. Many candidates were also observed to contain zinc finger domains, coiled-coiled domains, or loop-helix-loop domains, well-known regions for protein-protein interactions. One of the sequences identified was CLU. The CLU clone that was isolated from the yeast assay contained cDNA beginning at position 212 from the ATG site, thus lacking N-terminal 71 amino acids.

To further confirm the interaction between MMP-9 and CLU that was detected by yeast two hybrid screening, we performed GST pull down assay using recombinant GST-tagged MMP-9 fusion protein. The GST-MMP-9 was immobilized on a glutathione-agarose matrix and incubated with in vitro translated HA-tagged CLU (FIG. 1A) in the presence or absence of soluble bacterial lysate as a nonspecific competitor. Our results showed that MMP-9 and CLU still interacted even in the presence of the bacterial lysate, confirming the results from the yeast two hybrid system.

Figure 1:
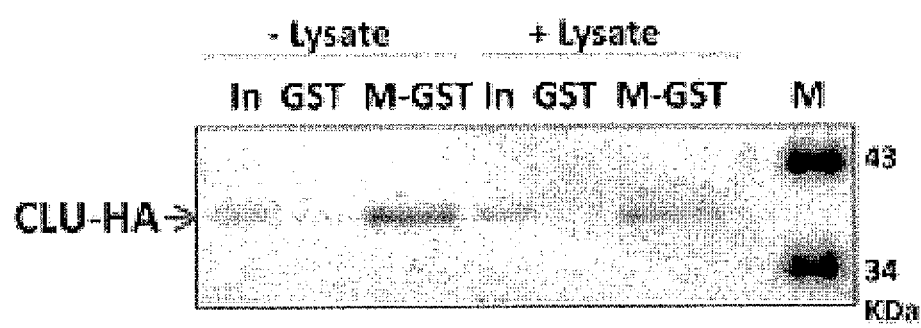
FIG. 1 shows that CLU binds to MMP-9 in vitro, not as an enzymatic substrate. (A) GST-tagged MMP-9 was purified from the bacterial cells transformed by the expression vector, and immobilized to the anti-GST-beads to prepare MMP-9-GST beads. Purified CLU-HA was incubated with MMP-9-GST beads (M-GST) or GST-beads (GST) in the presence (+Lysate) or absence (−Lysate) of bacterial lysate, followed by washing the beads with binding buffer. Bound proteins were resolved on denaturing 8% SDS/PAGE gel for the immunoblotting with anti-HA antibody. CLU cDNA detected in the yeast two hybrid assay, which corresponds to the CLU coding sequence beginning at position 212 from the ATG site, was used to produce a protein band of approximately 40 KDa. (B) Gelatin (20 µg) and CLU (2 µg) were mixed and incubated in the presence or absence of active MMP-9, followed by denaturing 12% SDS/PAGE gel electrophoresis, which then was stained with Coomasie blue. Two subunits of CLU are designated as α and β.
Figure 1:
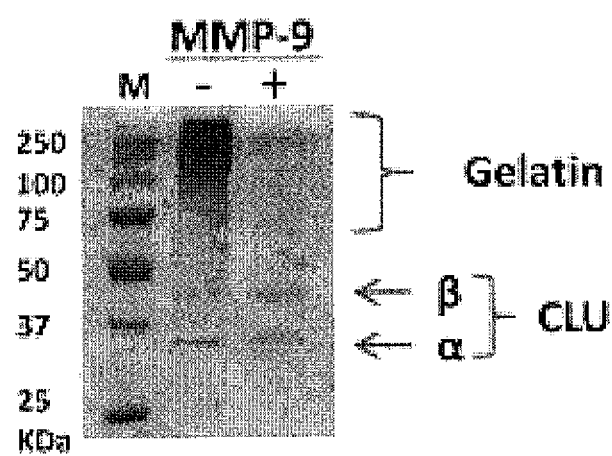

Next, as there are various known MMP-9 substrates, we tested a possibility that CLU might be a novel enzymatic substrate of MMP-9. To this end, in a preliminary experiment, we digested CLU with active MMP-9 to find that CLU was not digested by MMP-9. To confirm this, both CLU and gelatin, a known substrate for MMP-9, were incubated in the presence or absence of an excessive amount of active MMP-9, and then resolved on the denaturing SDS/PAGE gel followed by Coomasie staining (FIG. 1B). As shown on the gel, the density of CLU protein, separated as a and 6 subunits, changed little, whereas most high molecular weight gelatin disappeared upon incubation with MMP-9, indicating that CLU is not a substrate for MMP-9 in vitro.

Next, we tested whether MMP-9/CLU interaction also occurs in vivo. Using HEK293 cells, a human embryonic kidney cell line, mouse HA-tagged MMP-9 and Myc-tagged CLU expression vectors were transfected individually or in combination (FIG. 2A). Our results showed two protein bands corresponding to the full length unprocessed glycosylated form (~60 kDa) of CLU as well as processed CLU β-subunit (~37 kDa) upon immunoprecipitation (IP) with anti-HA antibody followed by immunoblotting with anti-Myc antibody when both CLU and MMP-9' were expressed together. CLU exists in the cytoplasm as ~50 kDa and ~60 KDa precursor forms (depending on the extent of glycosylation) of the secretory CLU [Trougakos, 2009]. We also recognized that a stronger band of ~50 KDa, compared with the other two IP lanes, was detected in co-transfected IP lane, which might be a non-glycosylated full-length form of CLU. Unfortunately, this band is overlapped with IgG heavy chain band from the antibodies used for IP. These results suggest that MMP-9 and CLU interact in vivo even before processing of the proteins. However, we failed to observe coimmunoprecipitation at the endogenous level using the HCLE whole cell extract; at present, we ascribed this failure to two possibilities, that antibodies used may interfere with and dissociate the interaction between of the two proteins, and/or that endogenous level of both proteins might not be enough to perform immunoprecipitation as both proteins are secreted immediately after their synthesis. As an alternative way to confirm their interaction in vivo, we localized the two proteins using confocal microscopy (FIG. 2B). In control without primary antibody incubation, neither MMP-9 nor CLU was localized. However, with specific antibodies both proteins were found to be present surrounding the nuclei, and the composite image of the two proteins indicated that both proteins are co-localized, probably in the secretory pathway (ER and/or Golgi compartment). The combined results of the in vitro binding assay, the IP, and confocal analysis suggest CLU and MMP-9 interact inside and outside cells.

Example 3

CLU Inhibits MMP-9 and MMP-2 Activity

Figure 3:
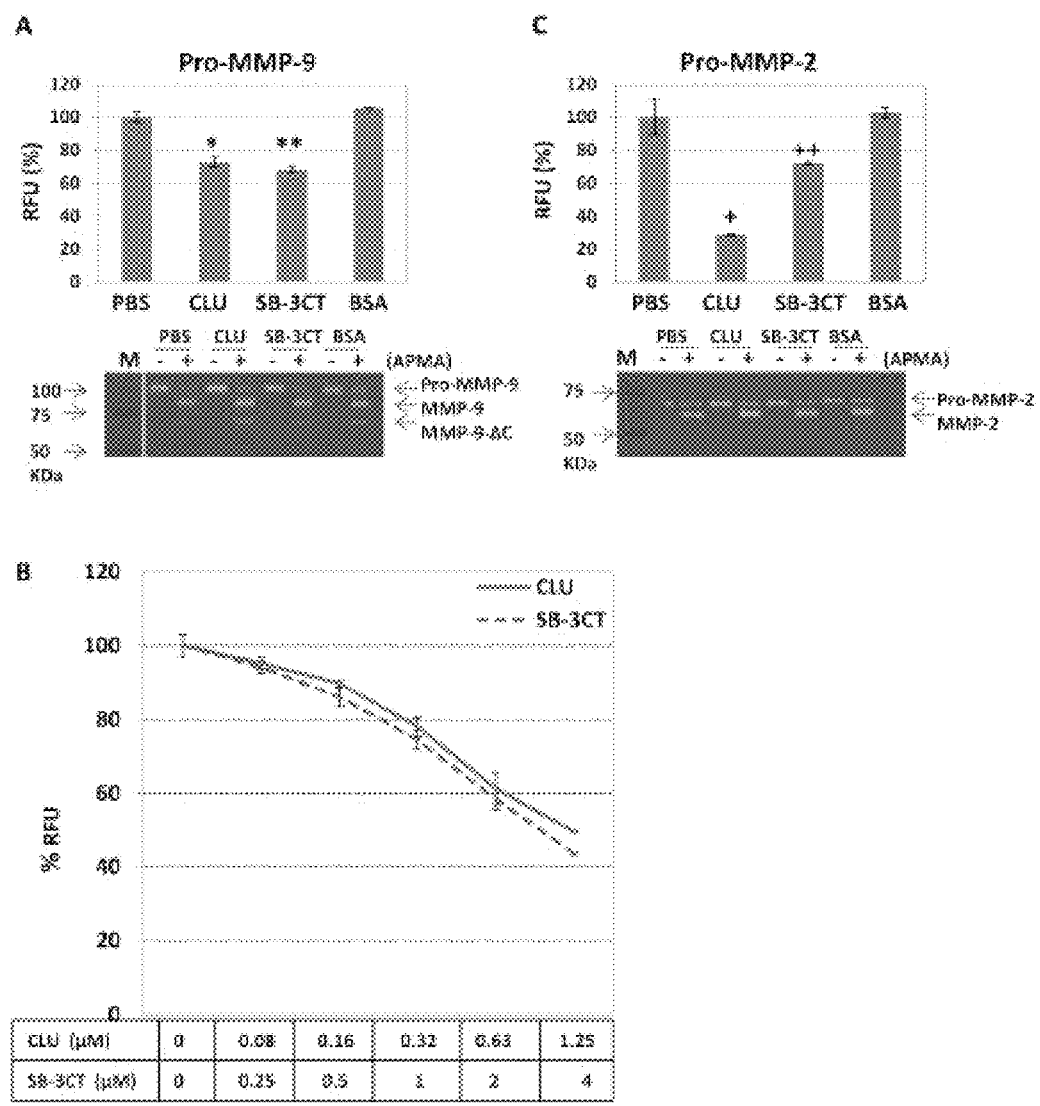
FIG. 3 shows that CLU inhibits MMP-9 and MMP-2 activities, without affecting APMA-induced MMP activation. Pro-MMP-9 (A) or pro-MMP-2 (C) was incubated with PBS, CLU (50 µg/ml, or 0.63 µM), SB3-CT (2 µM), or BSA (50 µg/ml), and MMP FRET substrate peptides in the presence and absence of 0.2 mM APMA at RT for 3 h. RFU, relative fluorescence unit, was obtained by considering the read out in PBS as 100%. Each reaction was performed in triplicate. Standard errors were depicted as a bar in each graph. Differences between values of PBS and CLU or SB-3CT reactions were statistically significant by Student t-test: *P=0.0004, **P=0.0001, +P=0.0003, and ++P=0.01. Gelatin zymography was performed with the samples pooled from each reaction set. Pro-MMPs, processed MMPs (MMP-9 or MMP-2), and C-terminal truncated, processed MMP-9 (MMP-9-ΔC) were indicated by arrows. (B) Dose-dependent inhibition of MMP-9 by CLU or SB-3CT was performed in the same condition.

Most MMPs are secreted as inactive pro-MMPs. The N-terminal propeptide blocks the catalytic domain by binding intramolecularly through the cysteine-zinc bridge between these two domains [Van Wart, 1990]. Enzyme activation occurs upon cleavage or processing of the propeptide domain [Van Wart, 1990; Chen, 1993]. To determine whether MMP-9/CLU interaction affects the cleavage process of the propeptide of MMP-9 and/or interferes with enzymatic activity of the processed active enzyme, we performed an in vitro MMP-9 inhibition assay, by adopting FRET assay using a fluorescence-quenched peptide substrate (FIG. 3A). In the presence of APMA the propeptide domain of pro-MMP is removed and thus it is activated in vitro [Visse, 2003]. APMA has also been shown to induce self-processing at a cryptic site at $Ala^{398}$-$Leu^{399}$ in the C-terminal region of the MMP-9 [Murphy, 1995]. We incubated pro-MMP-9 with PBS, CLU, SB-3CT, or BSA, and a fluorescence peptide substrate in the presence or absence of APMA. SB-3CT is a potent chemical inhibitor of gelatinases, MMP-2 and MMP-9, with Ki values in the sub-micromolar range [Kleifeld, 2001]. We monitored the change in fluorescence value during the incubation of the reactions up to 3 h, which reflects the enzymatic activity of APMA-activated MMPs. We did not see any apparent change in the fluorescence values' in the APMA-omitted reactions over the incubation time (data not shown), indicating that without APMA pro-MMP-9 could not get activated. At 3 h post incubation, the activity difference was read and reaction products were resolved by gelatin zymography. The results showed that CLU and SB-3CT inhibited the activity of MMP-9 by 28% and 32%, respectively, compared with PBS and BSA. Three independent experiments in triplicate each showed an average of 35% inhibition (p=0.002, student t-test) at 50 µg/ml of CLU (data not shown). When the processed enzyme products were resolved on the gel, three bands were detected in the APMA-treated samples, pro-MMP-9, propeptide-cleaved MMP-9 (MMP-9), and MMP-9 with both propeptide and C-terminal region cleaved (MMP-9-ΔC), whereas only pro-MMP-9 was detected in APMA-omitted samples. The extent of MMP-9 processing among the four reactions with APMA treatment was very similar, suggesting that CLU did not affect the enzyme processing by APMA. Thus, we suggest that CLU inhibit the enzymatic activity of MMP-9 without interfering with the APMA-induced processing of pro-MMP-9. It has been known that CLU is present at 50-100 g/ml in the human normal serum [Viard, 1999; Jenne, 1991]. We tested dose-dependent inhibition of MMP-9 with CLU or SB-3CT (FIG. 3B). The result showed that CLU is a stronger MMP-9 inhibitor than a synthetic gelatinase inhibitor, SB-3CT. In order to test the specificity of CLU/MMP-9 interaction, we also performed the inhibition assay with MMP2 (FIG. 3C). Our results showed that CLU inhibited MMP-2 activity by 72, %. The gel analysis indicated that the processing of MMP-2 was not altered among the different reactions, consistent with MMP-9 results. Comparison of extents of MMP-2 or -9 inhibition by CLU (50 µg/ml or 0.63 µM, MW=~80 KDa) and SB-3CT (1 µM) in FIG. 3B suggests that CLU is a more potent inhibitor of both MMP-9 and MMP-2 than SB-3CT.

Example 4

Inhibition of MMPs without a Hemopexin-Like Domain at the C-Terminus, Including MMP-7

Figure 4:
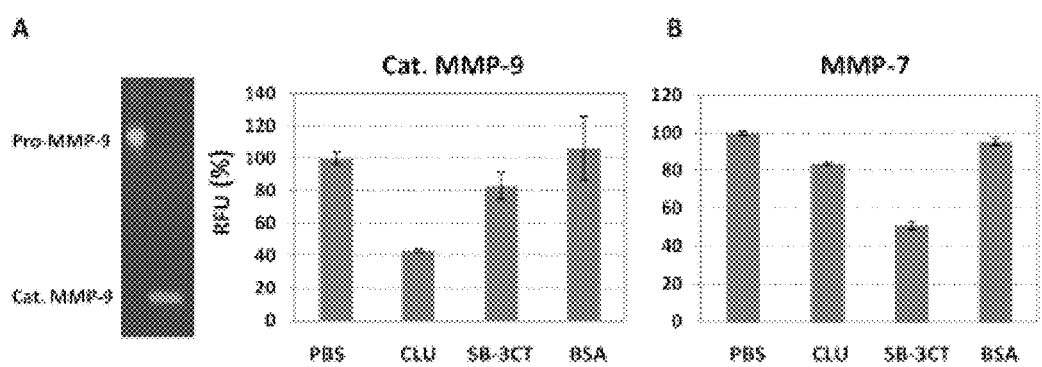
FIG. 4 shows that inhibition of MMP-9 by CLU does not require the C-terminal hemopexin-like domain. Recombinant MMP-9 catalytic domain (A) or APMA-activated MMP-7 (B) was incubated with PBS, CLU (50 µg/ml or 0.63 µM), SB3-CT (2 µM), or BSA (50 µg/ml), and MMP FRET substrate at RT for 0.3 h. RFU in PBS samples was considered 100%. Each reaction was performed in triplicate. Standard errors were depicted as a bar in each graph.

Most members of MMPs, except for MMP-7, MMP-23, and MMP-26, contain a hemopexin-like domain at the C-terminus of the enzyme, which modulates the processing and activity of the enzymes by serving as a binding region for regulatory or target proteins [Visse, 2003]. The initial binding assay above utilized the full length of active form of MMP-9. In order to refine the region important for the MMP-9/CLU interaction, we used MMP-9 catalytic domain, which lacks the C-terminal region encompassing the hemopexin-like domain (FIG. 4A). CLU inhibited MMP-9 activity by 59%, indicating that C-terminal region of MMP-9 is not required for inhibition. To further confirm our results, we tested MMP-7 which naturally lacks a C-terminal hemopexin-like domain (FIG. 4B). Our results showed that CLU inhibited APMA-activated MMP-7 by 17%, while SB-3CT (160 µM) by 49%, and both results were statistically significant. Together, our results indicate that CLU can inhibit the enzymatic activity of various members of MMPs, and does not depend on the C-terminal hemopexin-like domain for its function.

Example 5

CLU Enhances the Solubility of MMP-9 and MMP-2 in Hydrophobic Conditions

Figure 5:
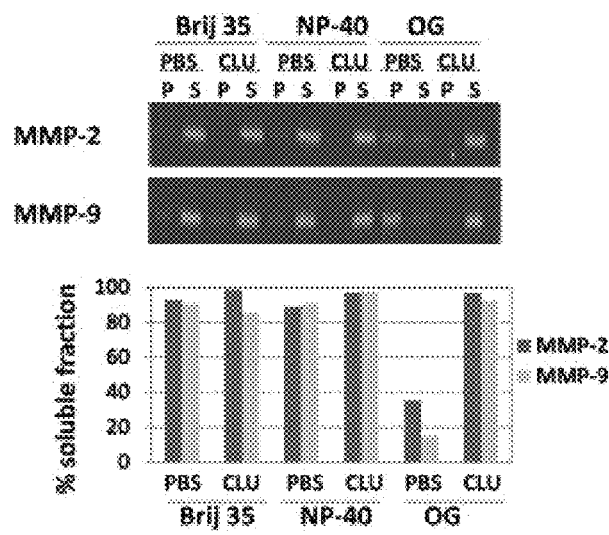
FIG. 5 shows that CLU enhances the solubility of MMP-9 and MMP-2. (A) Pro-MMP-2 or pro-MMP-9 was incubated in the buffer containing 0.04% of Brij 35, NP-40, or N-octyl glucopyranoside (OG) in the presence of CLU (C) or PBS (P), and then the soluble and insoluble fractions were obtained by centrifugation to resolve on the gelatin zymography. Relative soluble fraction was calculated by dividing the soluble density with total density of each set, obtained using Image J analysis. (B) Pro-MMP-2, (C) Pro-MMP-9 or APMA-processed active MMP-9 inhibition assays were performed in the reaction buffer containing 0.04% of Brij 35 or NP-40.
Figure 5:
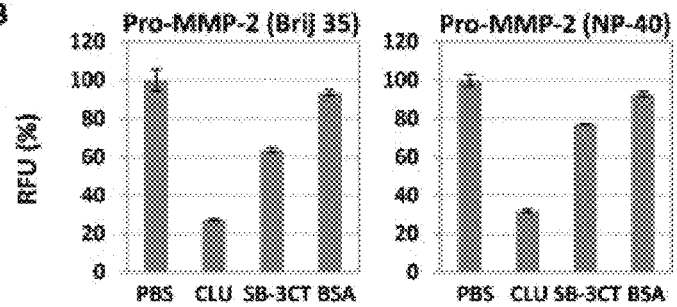
Figure 5:
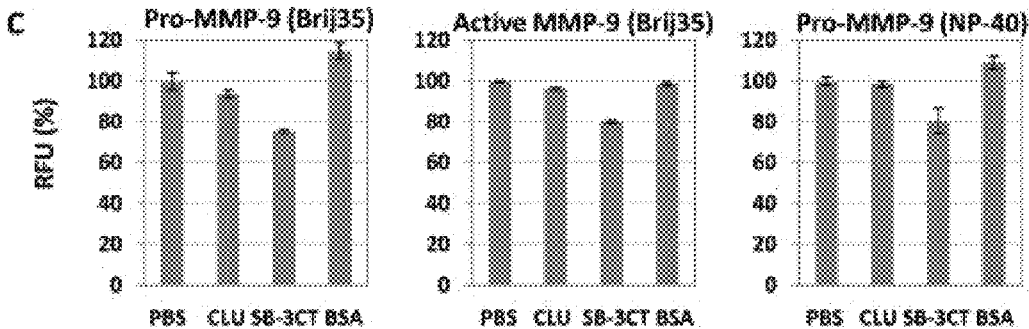

CLU interacts with various binding partners under different physiological conditions; however, the nature of their interaction is poorly understood. In order to assess the nature of the MMP-9/CLU interaction varying buffer conditions were investigated. In our experiments above (FIG. 3B), we used a low concentration of Brij 35 (0.002%). For our first experiment here we analyzed on the solubility of MMP2 and MMP-9 in three different nonionic detergents, Brij 35, NP-40, and N-octyl glucopyranoside (OG), at 0.04% in the presence or absence of CLU (FIG. 5A). The soluble and insoluble fractions were separated, and were resolved on the gelatin zymography. Our results indicated that Brij 35 and NP-40 showed no effect on the solubility of both MMP-2 and MMP-9 regardless of the presence of CLU. Interestingly, in the presence of OG the solubility of both enzymes decreased; however, OG failed to reduce their solubility in the presence of CLU. These results suggest a possibility that CLU may render pro-MMP-2 and MMP-9 soluble in certain hydrophobic conditions. Next, we performed the inhibition assay using pro-MMP-2 in the buffer containing 0.04% Brij 35 or NP-40. As shown in FIG. 5B, MMP-2 activity was inhibited by CLU in both buffers to the extent similar to that in the lower detergent concentration as shown in FIG. 3B. Furthermore, the level of inhibition shown by SB-3CT and BSA also revealed the similarity with that of a lower concentration of detergent, suggesting that MMP-2/CLU interaction may not be sensitive to the types or concentration of detergents. However, when the similar experiments were performed with pro-MMP-9 or APMA-activated MMP-9, the high concentration of Brij 35 or NP-40 did show little MMP-9 inhibition by CLU (FIG. 5C). These results indicate that high concentration of nonionic detergents may affect the ability of CLU to inhibit the MMP-9 but not MMP-2 activity.

Example 6

CLU Binds to Pro-MMP-9 with Higher Affinity than Processed MMP-9

Figure 6:
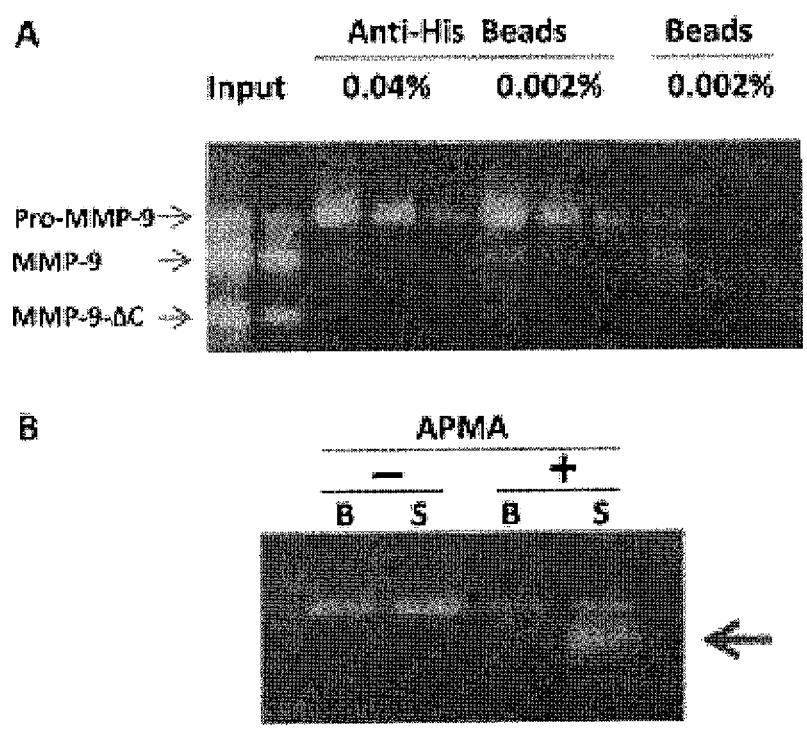
FIG. 6 shows that Pro-MMP-9 binds with higher affinity to CLU than processed MMP-9. (A) Recombinant proteins, Pro-MMP-9, MMP-9, MMP-9-ΔC, CLU-His were incubated together, and bound to agarose beads coupled or uncoupled with Anti-(His)$_6$ antibody in two different binding buffers containing Brij 35 concentrations, 0.04% or 0.002%. MMPs bound to the beads were obtained by washing with the corresponding binding buffer to resolve on gelatin zymography. Three different volumes of each sample were loaded to compare the relative density. (B) Pro-MMP-9 bound to CLU coupled to agarose beads, prepared as in (A), was incubated in the presence or absence of APMA for 1 h at RT, prior to separation of beads (B) and supernatant (S) fractions, which were resolved by zymography. Arrow indicates MMP-9 processed by APMA.

Since different detergent concentrations affected the extent of inhibition of MMP-9 activity by CLU, we tested whether detergents may influence the binding affinity of CLU for MMP-9. To test this possibility, CLU pull down assay was performed. Pro-MMP-9, MMP-9, and MMP-9-ΔC were mixed and incubated with CLU-His in two different concentrations of Brij 35. MMP-9 enzymes bound to CLU were isolated using anti-His tag antibody, and subjected to gelatin zymography to assess the relative amounts of different forms of MMP-9 (FIG. 6A). In the input lanes on the gel, the relative amount of pro-MMP9 was much lower than the other two forms of MMP-9. In contrast, lanes containing MMP-9 bound with CLU showed enrichment predominantly of pro-MMP-9 form compared with the densities of the other two forms. Analysis of the densities of individual bands using Image J software suggested that pro-MMP-9 may have at least 10 times stronger affinity for CLU than the other forms of MMP-9. The levels of pro-MMP-9 have little difference between low and high detergent concentrations, indicating the affinity is not sensitive to the detergent concentration. However, the amounts of MMP-9 and MMP-9-ΔC in the high Brij35 concentration were much lower than those in the low concentration and similar to those in beads control, suggesting that MMP-9 and MMP-9-ΔC do not bind to CLU at the high Brij 35 concentration, consistent with the failure of CLU inhibition of MMP-9 activity in that condition.

The above results suggest that the propeptide domain is essential for high affinity binding of CLU with pro-MMP-9. To confirm this further, we cleaved pro-MMP-9 bound to CLU on beads with APMA, and separated supernatant and bead fractions (FIG. 6B). We reasoned that if CLU binds to the propeptide domain, the processed active form of MMP-9 should be enriched in supernatant fraction (S), and, if it binds to the other part of the enzyme, the processed enzyme should be in the beads fraction (B). When the samples were resolved on the gel, pro-MMP-9 was equally distributed into S and B fractions in the untreated reaction, suggesting the release of portion of enzymes from the beads into solution during the incubation. However, in APMA-treated reaction, a large fraction of the processed MMP-9 was detected only in the S fraction, indicating a greater affinity at the propeptide domain of MMP-9, with a lower affinity binding sites located elsewhere.

Example 7

CLU Expression in the Human Corneal Epithelial Cells

To determine how human corneal epithelial cells express and secrete the CLU protein, we used an immortalized human corneal epithelial cell line (HCLE) that was kindly provided by Dr. Ilene Gipson (Harvard University).

We isolated total RNA from the HCLE cells as well as from human corneal epithelial tissue and human periodontal ligament stem cells for the synthesis of cDNA. This cDNA was then used for PCR amplification with three different sets of primers designed previously in order to detect the three different isoforms of CLU transcripts (Andersen et al., 2007) (FIG. 8A), presumably transcribed by three different transcriptional initiation sites (Cochrane et al., 2007). Form 1 (isoform1) is for the transcript of NM_001831, and form 2 (isoform2), for NM_203339 in the GeneBank DNA data base.

While all three transcript isoforms produce the secreted form of CLU, only transcript isoform 1 has a potential to produce the transcripts lacking exon 2 which can be translated into the nuclear CLU protein (Leskov et al., 2003). Our results indicate that HCLEs and corneal epithelial cells express isoform 1 as a dominant transcript. HCLE cells, however, also express transcript isoforms 2 and 3 while human corneal epithelial cells only express transcript isoform 1. This difference may be due to the difference between cultured cells and fresh tissue. Culturing of human corneal epithelial cells may induce the expression of transcript isoforms 2 and 3. There was no significant difference observed between the densities of isoforms 1 and 2 in the periodontal stem cells. Overexpression of isoform 2 was shown to render certain prostate cells more resistant to Fas-mediated cell death (Miyake et al., 2001).

FIG. 8B shows that CLU is secreted into culture media from the corneal cells. Briefly, the media from the HCLE cell culture was subject to Western blotting with an anti-CLU antibody (Santa Cruz Biotech., sc-6419). Lane 1 contains conditioned medium (K-sfm) from the cell culture; lane 2 has regular medium (K-sfm plus BPE and EGF) from the culture; and lane 3 includes fresh regular medium as a control. The arrow indicates the position of the β-subunit of CLU with the expected size of ~40 KD.

Example 8

CLU Processing is Influenced by Growth Conditions

To test if there are any changes in CLU expression and processing in response to the different growth conditions, we altered cell culture conditions. We grew the HCLE cells to a subconfluent cell density or kept them at a confluent cell density so that they underwent contact inhibition in the regular K-sfm medium. We also induced stratification of the corneal cells by replacing the regular medium with DMEM:F12 medium for the confluent cells (FIG. 9) (Gipson et al., 2003). The distribution of the intracellular CLU protein undergoing processing was not influenced by the cell density (subconfluent vs. confluent) but was affected by different media (K-sfm vs. DMEM:F12), which showed that CLU intermediate protein bands increased or decreased in the stratified cell culture. The data suggests that the environmental factors affecting the corneal cells may alter the production or processing of mature CLU protein in cells.

Accumulating evidence supports the concept that MMP-9 is disease-promoting whereas CLU is preventive in situations involving inflammatory processes. We found that MMP-9 and CLU interact with each other inside and outside cells. We showed that co-expression of MMP-9 and CLU delays the intracellular processing of the CLU proteins, and that CLU inhibits MMP-9 activity in vitro. The current observations suggest that MMP-9 and CLU may influence each other's regulation and activity in an antagonistic manner, so there may be opposing roles for MMP-9 and CLU in the progression and development of inflammatory disease such as dry eye.

Our experiments show that CLU is expressed by corneal epithelial cells and binds to and inhibits MMPs, which are known to be involved in wound progression and symptoms of dry eye disease. Therefore, CLU can be used as a biomarker for the disease progression as well as a therapeutic agent for the prevention and treatment of dry eye and promotion of wound healing.

Example 9

Clusterin Inhibits the Induction of MMP-9 by TNF-Alpha from Human Corneal Limbal Epithelial (HCLE) Cells TNF (tumor necrosis factor)-alpha is one of key cytokines involved in inflammatory events. MMP (matrix metalloproteinase)-9 also plays a role in the pathological inflammatory process. TNF-alpha is known to induce MMP-9 from certain cell types such as HCLE cells.

HCLE cells were grown to be confluent in KSFM media and then replenished with DMAM/F12 media to stratify cells for 7 days. To these cells in serum-free DMEM/F12 media, clusterin (50 ug/ml), bovine serum albumin (BSA, 50 ug/ml), and TNF-alpha (10 ng/ml), individually or in combination, were treated for 24 hours. The same volume of supernatants of the cell cultures treated were collected to resolve on SDS/PAGE gel containing gelatin in order to perform gelatin zymography to visualize the presence of MMP-9 secreted from the cells. When compared with untreated (Un), MMP-9 density increased upon TNF treatment (TNF), indicating that TNF induced MMP-9 secretion from the cells. However, when TNF was treated with CLU (TNF+CLU) did not increase MMP-9 secretion any longer, suggesting that CLU inhibited TNF-induced MMP-9 secretion. Therefore, Clusterin inhibits the induction of MMP-9 from human corneal limbal epithelial (HCLE) cells. (See FIG. 10)

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It should be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It should be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein, including but not limited to patents, patent applications, and non-patent literature, are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Those skilled in the art will recognize, or be able to ascertain using no more than routine experimentation, many equivalents to the specific embodiments of the method and compositions described herein. Such equivalents are intended to be encompassed by the following claims.

REFERENCES

Afonso, A. A., Sobrin, L., Monroy, D. C., Selzer, M., Lokeshwar, B. and Pflugfelder, S. C. Tear fluid gelatinase B activity correlates with IL-1alpha concentration and fluorescein clearance in ocular rosacea. *Invest Ophthalmol Vis Sci* 40 (1999), pp. 2506-12.

Ammar, H. and Closset, J. L. CLU activates survival through the phosphatidylinositol 3-kinase/Akt pathway. *J Biol Chem* 283 (2008), pp. 12851-61.

Andersen, C. L., Schepeler, T., Thorsen, K., Birkenkamp-Demtroder, K., Mansilla, F., Aaltonen, L. A., Laurberg, S. and Orntoft, T. F. CLU expression in normal mucosa and colorectal cancer. *Mol Cell Proteomics* 6 (2007), pp. 1039-48.

Aronow, B. J., Lund, S. D., Brown, T. L., Harmony, J. A. and Witte, D. P. Apolipoprotein J expression at fluid-tissue interfaces: potential role in barrier cytoprotection. *Proc Natl Acad Sci USA* 90 (1993), pp. 725-9.

Bayon, Y., Ortiz, M. A., Lopez-Hernandez, F. J., Howe, P. H. and Piedrafita, F. J. The retinoid antagonist MX781 induces CLU expression in prostate cancer cells via heat shock factor-1 and activator protein-1 transcription factors. *Cancer Res* 64 (2004), pp. 5905-12.

Burkey, B. F., deSilva, H. V. and Harmony, J. A. Intracellular processing of apolipoprotein J precursor to the mature heterodimer. *J Lipid Res* 32 (1991), pp. 1039-48.

Calero, M., Rostagno, A., Matsubara, E., Zlokovic, B., Frangione, B. and Ghiso, J. Apolipoprotein J (CLU) and Alzheimer's disease. *Microsc Res Tech* 50 (2000), pp. 305-15.

Calkins, C. M., Bensard, D. D., Shames, B. D., Pulido, E. J., Abraham, E., Fernandez, N., Meng, X., Dinarello, C. A. and McIntyre, R. C., Jr. IL-1 regulates in vivo C—X—C chemokine induction and neutrophil sequestration following endotoxemia. *J Endotoxin Res* 8 (2002), pp. 59-67.

Cervellera, M., Raschella, G., Santilli, G., Tanno, B., Ventura, A., Mancini, C., Sevignani, C., Calabretta, B. and Sala, A. Direct transactivation of the anti-apoptotic gene apolipoprotein J (CLU) by B-MYB. *J Biol Chem* 275 (2000), pp. 21055-60.

Charnay, Y., Imhof, A., Vallet, P. G., Hakkoum, D., Lathuiliere, A., Poku, N., Aronow, B., Kovari, E., Bouras, C. and Giannakopoulos, P. CLU expression during fetal and postnatal CNS development in mouse. *Neuroscience* 155 (2008), pp. 714-24.

Chen, Y., Lim, B. K., Peh, S. C., Abdul-Rahman, P. S. and Hashim, O. H. Profiling of serum and tissue high abundance acute-phase proteins of patients with epithelial and germ line ovarian carcinoma. *Proteome Sci* 6 (2008a), p. 20.

Chen, Z., Tong, L., Li, Z., Yoon, K. C., Qi, H., Farley, W., Li, D. Q. and Pflugfelder, S. C. Hyperosmolarity-induced cornification of human corneal epithelial cells is regulated by JNK MAPK. *Invest Ophthalmol Vis Sci* 49 (2008b), pp. 539-49.

Chung, J., Kwak, C., Jin, R. J., Lee, C. H., Lee, K. H. and Lee, S. E. Enhanced chemosensitivity of bladder cancer cells to cisplatin by suppression of CLU in vitro. *Cancer Lett* 203 (2004), pp. 155-61.

Cochrane, D. R., Wang, Z., Muramaki, M., Gleave, M. E. and Nelson, C. C. Differential regulation of CLU and its isoforms by androgens in prostate cells. *J Biol Chem* 282 (2007), pp. 2278-87.

Criswell, T., Beman, M., Araki, S., Leskov, K., Cataldo, E., Mayo, L. D. and Boothman, D. A. Delayed activation of insulin-like growth factor-1 receptor/Src/MAPKI/Egr-1 signaling regulates CLU expression, a pro-survival factor. *J Biol Chem* 280 (2005), pp. 14212-21.

de Silva, H. V., Stuart, W. D., Park, Y. B., Mao, S. J., Gil, C. M., Wetterau, J. R., Busch, S. J. and Harmony, J. A. Purification and characterization of apolipoprotein J. *J Biol Chem* 265 (1990), pp. 14292-7.

Fini, M. E., Parks, W. C., Rinehart, W. B., Girard, M. T., Matsubara, M., Cook, J. R., West-Mays, J. A., Sadow, P. M., Burgeson, R. E., Jeffrey, J. J., Raizman, M. B., Krueger, R. R. and Zieske, J. D. Role of matrix metalloproteinases in failure to re-epithelialize after corneal injury. *Am J Pathol* 149 (1996), pp. 1287-302.

Fox, R. I., Stern, M. and Michelson, P. Update in Sjogren syndrome. *Curr Opin Rheumatol* 12 (2000), pp. 391-8.

Gipson, I. K., Spurr-Michaud, S., Argueso, P., Tisdale, A., Ng, T. F. and Russo, C. L. Mucin gene expression in immortalized human corneal-limbal and conjunctival epithelial cell lines. *Invest Ophthalmol Vis Sci* 44 (2003), pp. 2496-506.

Gu, Z., Cui, J., Brown, S., Fridman, R., Mobashery, S., Strongin, A. Y. and Lipton, S. A. A highly specific inhibitor of matrix metalloproteinase-9 rescues laminin from proteolysis and neurons from apoptosis in transient focal cerebral ischemia. *J Neurosci* 25 (2005), pp. 6401-8.

Hogasen, K., Mollnes, T. E., Harboe, M., Gotze, O., Hammer, H. B. and Oppermann, M. Terminal complement pathway activation and low lysis inhibitors in rheumatoid arthritis synovial fluid. *J Rheumatol* 22 (1995), pp. 24-8.

Leskov, K. S., Klokov, D. Y., Li, J., Kinsella, T. J. and Boothman, D. A. Synthesis and functional analyses of nuclear CLU, a cell death protein. *J Biol Chem* 278 (2003), pp. 11590-600.

Li, D. Q., Chen, Z., Song, X. J., Luo, L. and Pflugfelder, S. C. Stimulation of matrix metalloproteinases by hyperosmolarity via a JNK pathway in human corneal epithelial cells. *Invest Ophthalmol Vis Sci* 45 (2004), pp. 4302-11.

Li, D. Q., Lokeshwar, B. L., Solomon, A., Monroy, D., Ji, Z. and Pflugfelder, S. C. Regulation of MMP-9 production by human corneal epithelial cells. *Exp Eye Res* 73 (2001), pp. 449-59.

Li, D. Q., Luo, L., Chen, Z., Kim, H. S., Song, X. J. and Pflugfelder, S. C. JNK and ERK MAP kinases mediate induction of IL-1beta, TNF-alpha and IL-8 following hyperosmolar stress in human limbal epithelial cells. *Exp Eye Res* 82 (2006), pp. 588-96.

Luo, L., Li, D. Q., Corrales, R. M. and Pflugfelder, S. C. Hyperosmolar saline is a proinflammatory stress on the mouse ocular surface. *Eye Contact Lens* 31 (2005), pp. 186-93.

Matsuda, A., Itoh, Y., Koshikawa, N., Akizawa, T., Yana, I. and Seiki, M. CLU, an abundant serum factor, is a possible negative regulator of MT6-MMP/MMP-25 produced by neutrophils. *J Biol Chem* 278 (2003), pp. 36350-7.

McLaughlin, L., Zhu, G., Mistry, M., Ley-Ebert, C., Stuart, W. D., Florio, C. J., Groen, P. A., Witt, S. A., Kimball, T. R., Witte, D. P., Harmony, J. A. and Aronow, B. J. Apolipoprotein J/CLU limits the severity of murine autoimmune myocarditis. *J Clin Invest* 106 (2000), pp. 1105-13.

Miyake, H., Hara, S., Zellweger, T., Kamidono, S., Gleave, M. E. and Hara, I. Acquisition of resistance to Fas-mediated apoptosis by overexpression of CLU in human renal-cell carcinoma cells. *Mol Urol* 5 (2001), pp. 105-11.

Mohan, R., Chintala, S. K., Jung, J. C., Villar, W. V., McCabe, F., Russo, L. A., Lee, Y., McCarthy, B. E., Wollenberg, K. R., Jester, J. V., Wang, M., Welgus, H. G., Shipley, J. M., Senior, R. M. and Fini, M. E. Matrix metalloproteinase gelatinase B (MMP-9) coordinates and effects epithelial regeneration. *J Biol Chem* 277 (2002), pp. 2065-72.

Nakamura, S., Shibuya, M., Nakashima, H., Hisamura, R., Masuda, N., Imagawa, T., Uehara, M. and Tsubota, K. Involvement of oxidative stress on corneal epithelial alterations in a blink-suppressed dry eye. *Invest Ophthalmol Vis Sci* 48 (2007), pp. 1552-8.

Newkirk, M. M., Apostolakos, P., Neville, C. and Fortin, P. R. Systemic lupus erythematosus, a disease associated with low levels of CLU/apoJ, an antiinflammatory protein. *J Rheumatol* 26 (1999), pp. 597-603.

Pflugfelder, S. C., de Paiva, C. S., Li, D. Q. and Stern, M. E. Epithelial-immune cell interaction in dry eye. *Cornea* 27 Suppl 1 (2008), pp. S9-11.

Pflugfelder, S. C., Farley, W., Luo, L., Chen, L. Z., de Paiva, C. S., Olmos, L. C., Li, D. Q. and Fini, M. E. Matrix metalloproteinase-9 knockout confers resistance to corneal epithelial barrier disruption in experimental dry eye. *Am J Pathol* 166 (2005), pp. 61-71.

Pucci, S., Bonanno, E., Pichiorri, F., Angeloni, C. and Spagnoli, L. G. Modulation of different CLU isoforms in human colon tumorigenesis. *Oncogene* 23 (2004), pp. 2298-304.

Reddy, K. B., Jin, G., Karode, M. C., Harmony, J. A. and Howe, P. H. Transforming growth factor beta (TGF beta)-induced nuclear localization of apolipoprotein J/CLU in epithelial cells. *Biochemistry* 35 (1996), pp: 6157-63.

Rosenberg, M. E., Girton, R., Finkel, D., Chmielewski, D., Barrie, A., 3rd, Witte, D. P., Zhu, G., Bissler, J. J., Harmony, J. A. and Aronow, B. J. Apolipoprotein J/CLU prevents a progressive glomerulopathy of aging. *Mol Cell Biol* 22 (2002), pp. 1893-902.

Sallman, D. A., Chen, X., Zhong, B., Gilvary, D. L., Zhou, J., Wei, S. and Djeu, J. Y. CLU mediates TRAIL resistance in prostate tumor cells. *Mol Cancer Ther* 6 (2007), pp. 2938-47.

Santilli, G., Aronow, B. J. and Sala, A. Essential requirement of apolipoprotein J (CLU) signaling for IkappaB expression and regulation of NF-kappaB activity. *J Biol Chem* 278 (2003), pp. 38214-9.

Savkovic, V., Gantzer, H., Reiser, U., Selig, L., Gaiser, S., Sack, U., Kloppel, G., Mossner, J., Keim, V., Horn, F. and Bodeker, H. CLU is protective in pancreatitis through anti-apoptotic and anti-inflammatory properties. *Biochem Biophys Res Commun* 356 (2007), pp. 431-7.

Schaumberg, D. A., Sullivan, D. A., Buring, J. E. and Dana, M. R. Prevalence of dry eye syndrome among US women. *Am J Ophthalmol* 136 (2003), pp. 318-26.

Schonbeck, U., Mach, F. and Libby, P. Generation of biologically active IL-1 beta by matrix metalloproteinases: a novel caspase-1-independent pathway of IL-1 beta processing. *J Immunol* 161 (1998), pp. 3340-6.

Selvan, R. S., Kapadia, H. B. and Platt, J. L. Complement-induced expression of chemokine genes in endothelium: regulation by IL-1-dependent and -independent mechanisms. *J Immunol* 161 (1998), pp. 4388-95.

Sensibar, J. A., Sutkowski, D. M., Raffo, A., Buttyan, R., Griswold, M. D., Sylvester, S. R., Kozlowski, J. M. and Lee, C. Prevention of cell death induced by tumor necrosis factor alpha in LNCaP cells by overexpression of sulfated glycoprotein-2 (CLU). *Cancer Res* 55 (1995), pp. 2431-7.

Shannan, B., Seifert, M., Leskov, K., Willis, J., Boothman, D., Tilgen, W. and Reichrath, J. Challenge and promise: roles for CLU in pathogenesis, progression and therapy of cancer. *Cell Death Differ* 13 (2006), pp. 12-9.

Sharma, A., Bhattacharya, B., Puri, R. K. and Maheshwari, R. K. Venezuelan equine encephalitis virus infection causes modulation of inflammatory and immune response genes in mouse brain. *BMC Genomics* 9 (2008), p. 289.

Solomon, A., Dursun, D., Liu, Z., Xie, Y., Macri, A. and Pflugfelder, S. C. Pro- and anti-inflammatory forms of interleukin-1 in the tear fluid and conjunctiva of patients with dry-eye disease. *Invest Ophthalmol Vis Sci* 42 (2001), pp. 2283-92.

Stern, M. E., Gao, J., Siemasko, K. F., Beuerman, R. W. and Pflugfelder, S. C. The role of the lacrimal functional unit in the pathophysiology of dry eye. *Exp Eye Res* 78 (2004), pp. 409-16.

Takase, O., Minto, A. W., Purl, T. S., Cunningham, P. N., Jacob, A., Hayashi, M. and Quigg, R. J. Inhibition of NF-kappaB-dependent Bcl-xL expression by CLU promotes albumin-induced tubular cell apoptosis. *Kidney Int* 73 (2008), pp. 567-77.

Tessier, P. A., Naccache, P. H., Clark-Lewis, I., Gladue, R. P., Neote, K. S. and McColl, S. R. Chemokine networks in vivo: involvement of C—X—C and C—C chemokines in neutrophil extravasation in vivo in response to TNF-alpha. *J Immunol* 159 (1997), pp. 3595-602.

Tomlinson, A., Khanal, S., Ramaesh, K., Diaper, C. and McFadyen, A. Tear film osmolarity: determination of a referent for dry eye diagnosis. *Invest Ophthalmol Vis Sci* 47 (2006), pp. 4309-15.

Wilson, M. R. and Easterbrook-Smith, S. B. CLU is a secreted mammalian chaperone. *Trends Biochem Sci* 25 (2000), pp. 95-8.

Woessner, J. F., Jr. Matrix metalloproteinases and their inhibitors in connective tissue remodeling. *FASEB J* 5 (1991), pp. 2145-54.

Wong, P., Pfeffer, B. A., Bernstein, S. L., Chambers, M. L., Chader, G. J., Zakeri, Z. F., Wu, Y. Q., Wilson, M. R. and Becerra, S. P. CLU protein diversity in the primate eye. *Mol Vis* 6 (2000), pp. 184-91.

Yang, C. R., Leskov, K., Hosley-Eberlein, K., Criswell, T., Pink, J. J., Kinsella, T. J. and Boothman, D. A. Nuclear CLU/XIP8, an x-ray-induced Ku70-binding protein that signals cell death. *Proc Natl Acad Sci USA* 97 (2000), pp. 5907-12.

Yeh, S., Song, X. J., Farley, W., Li, D. Q., Stern, M. E. and Pflugfelder, S. C. Apoptosis of ocular surface cells in experimentally induced dry eye. *Invest Ophthalmol Vis Sci* 44 (2003), pp. 124-9.

Zhang, F., Sha, J., Wood, T. G., Galindo, C. L., Garner, H. R., Burkart, M. F., Suarez, G., Sierra, J. C., Agar, S. L., Peterson, J. W. and Chopra, A. K. Alteration in the activation state of new inflammation-associated targets by phospholipase A2-activating protein (PLAA). *Cell Signal* 20 (2008), pp. 844-61.

Zhang, H., Kim, J. K., Edwards, C. A., Xu, Z., Taichman, R. and Wang, C. Y. CLU inhibits apoptosis by interacting with activated Bax. *Nat Cell Biol* 7 (2005), pp. 909-15.

VanSaun, M. N., and Matrisian, L. M. (2006) *Birth Defects Res C Embryo Today* 78, 69-79

Lemaitre, V., and D'Armiento, J. (2006) *Birth Defects Res C Embryo Today* 78, 1-10

Parks, W. C., and Shapiro, S. D. (2001) *Respir Res* 2, 10-19

Hahn-Dantona, E., Ruiz, J. F., Bornstein, P., and Strickland, D. K. (2001) *J Biol Chem* 276, 15498-15503

Visse, R., and Nagase, H. (2003) *Circ Res* 92, 827-839

Chakraborti, S., Mandal, M., Das, S., Mandal, A., and Chakraborti, T. (2003) *Mol Cell Biochem* 253, 269-285

Luo, L., Li, D. Q., Doshi, A., Farley, W., Corrales, R. M., and Pflugfelder, S. C. (2004) *Invest Ophthalmol Vis Sci* 45, 4293-4301

Song, X. J., Li, D. Q., Farley, W., Luo, L. H., Heuckeroth, R. O., Milbrandt, J., and Pflugfelder, S. C. (2003) *Invest Ophthalmol Vis Sci* 44, 4223-4229

Chotikavanich, S., de Paiva, C. S., Li de, Q., Chen, J. J., Bian, F., Farley, W. J., and Pflugfelder, S. C. (2009) *Invest Ophthalmol Vis Sci* 50, 3203-3209

Matsubara, M., Zieske, J. D., and Fini, M. E. (1991) *Invest Ophthalmol Vis Sci* 32, 3221-3237

Shannan, B., Seifert, M., Leskov, K., Willis, J., Boothman, D., Tilgen, W., and Reichrath, J. (2006) *Cell Death Differ* 13, 12-19

Nishida, K., Kawasaki, S., Adachi, W., and Kinoshita, S. (1996) *Invest Ophthalmol Vis Sci* 37, 2285-2292

Argueso, P., Tisdale, A., Spurr-Michaud, S., Sumiyoshi, M., and Gipson, I. K. (2006) *Invest Ophthalmol Vis Sci* 47, 113-119

Gordon, G. M., Ledee, D. R., Feuer, W. J., and Fini, M. E. (2009) *J Cell Physiol* 221, 402-411

Murphy, G., and Crabbe, T. (1995) *Methods Enzymol* 248, 470-484

Trougakos, I. P., Djeu, J. Y., Gonos, E. S., and Boothman, D. A. (2009) *Cancer Res* 69, 403-406

Van Wart, H. E., and Birkedal-Hansen, H. (1990) *Proc Natl Acad Sci USA* 87, 5578-5582

Chen, L. C., Noelken, M. E., and Nagase, H. (1993) *Biochemistry* 32, 10289-10295

Kleifeld, O., Kotra, L. P., Gervasi, D. C., Brown, S., Bernardo, M. M., Fridman, R., Mobashery, S., and Sagi, I. (2001) *J Biol Chem* 276, 17125-17131

Viard, I., Wehrli, P., Jornot, L., Bullani, R., Vechietti, J. L., Schifferli, J. A., Tschopp, J., and French, L. E. (1999) *J Invest Dermatol* 112, 290-296

Jenne, D. E., Lowin, B., Peitsch, M. C., Bottcher, A., Schmitz, G., and Tschopp, J. (1991) *J Biol Chem* 266, 11030-11036

Yi, X., Wang, Y., and Yu, F. S. (2000) *Invest Ophthalmol Vis Sci* 41, 4093-4100

Asahi, M., Wang, X., Mori, T., Sumii, T., Jung, J. C., Moskowitz, M. A., Fini, M. E., and Lo, E. H. (2001) *J Neurosci* 21, 7724-7732

Behzadian, M. A., Wang, X. L., Windsor, L. J., Ghaly, N., and Caldwell, R. B. (2001) *Invest Ophthalmol Vis Sci* 42, 853-859

Maskos, K., and Bode, W. (2003) *Mol Biotechnol* 25, 241-266

O'Connell, J. P., Willenbrock, F., Docherty, A. J., Eaton, D., and Murphy, G. (1994) *J Biol Chem* 269, 14967-14973

Fujimoto, N., Terlizzi, J., Aho, S., Brittingham, R., Fertala, A., Oyama, N., McGrath, J. A., and Uitto, J. (2006) *Exp Dermatol* 15, 300-307

Monferran, S., Paupert, J., Dauvillier, S., Salles, B., and Muller, C. (2004) *EMBO J* 23, 3758-3768

Yan, L., Borregaard, N., Kjeldsen, L., and Moses, M. A. (2001) *J Biol Chem* 276, 37258-37265

Gerngross, T. U. (2004) *Nat Biotechnol* 22, 1409-1414

Silkensen, J. R., Skubitz, A. P., Skubitz, K. M., and Rosenberg, M. E. (1999) *J Pept Res* 54, 449-457

Lakins, J. N., Poon, S., Easterbrook-Smith, S. B., Carver, J. A., Tenniswood, M. P., and Wilson, M. R. (2002) *Biochemistry* 41, 282-291

Yang, Z., Strickland, D. K., and Bornstein, P. (2001) *J Biol Chem* 276, 8403-8408

Van den Steen, P. E., Van Aelst, I., Hvidberg, V., Piccard, H., Fiten, P., Jacobsen, C., Moestrup, S. K., Fry, S., Royle, L., Wormald, M. R., Wallis, R., Rudd, P. M., Dwek, R. A., and Opdenakker, G. (2006) *J Biol Chem* 281, 18626-18637

Barmina, O. Y., Walling, H. W., Fiacco, G. J., Freije, J. M., Lopez-Otin, C., Jeffrey, J. J., and Partridge, N. C. (1999) *J Biol Chem* 274, 30087-30093

Kounnas, M. Z., Loukinova, E. B., Stefansson, S., Harmony, J. A., Brewer, B. H., Strickland, D. K., and Argraves, W. S. (1995) *J Biol Chem* 270, 13070-13075

Hsu, Y. T., and Youle, R. J. (1997) *J Biol Chem* 272, 13829-13834

Hsu, Y. T., and Youle, R. J. (1998) *J Biol Chem* 273, 10777-10783

Chadli, A., Ladjimi, M. M., Baulieu, E. E., and Catelli, M. G. (1999) *J Biol Chem* 274, 4133-4139

Tan, Y. J., and Ting, A. E. (2000) *Protein Eng* 13, 887-892

Bartl, M. M., Luckenbach, T., Bergner, O., Ullrich, O., and Koch-Brandt, C. (2001) *Exp Cell Res* 271, 130-141

Sobrin, L., Liu, Z., Monroy, D. C., Solomon, A., Selzer, M. G., Lokeshwar, B. L., and Pflugfelder, S. C. (2000) *Invest Ophthalmol Vis Sci* 41, 1703-1709

Kobayashi, T., Kishimoto, J., Ge, Y., Jin, W., Hudson, D. L., Ouahes, N., Ehama, R., Shinkai, H., and Burgeson, R. E. (2001) *EMBO Rep* 2, 604-608

Pi, J., Diwan, B. A., Sun, Y., Liu, J., Qu, W., He, Y., Styblo, M., and Waalkes, M. P. (2008) *Free Radic Biol Med* 45, 651-658

Nakamura, T., Nishida, K., Dota, A., and Kinoshita, S. (2002) *Invest Ophthalmol Vis Sci* 43, 1702-1707

Corrales, R. M., Stern, M. E., De Paiva, C. S., Welch, J., Li, D. Q., and Pflugfelder, S. C. (2006) *Invest Ophthalmol Vis Sci* 47, 3293-3302

Brinckerhoff, C. E., Matrisian, L. M. (2002) *Nature Reviews Mol. Cell Biology*, Vol. 3, March 2002, 207-214.

Wielockx, B., Libert, C., Wilson, C. (2004) *Cytokine and Growth Factor Reviews* 15, 111-115.

Corbel, M. Belleguic, C., Boichot, E., Lagente, V. (2002) *Cell Biology and Toxicology* 18:51-61.

---

What is claimed is:

1. A method of treating dry eye disease or an ocular surface of an eye at risk for dry eye disease comprising: topically administering to a patient in need thereof having an eye with an intact ocular surface a pharmaceutical composition comprising an isolated fragment of clusterin, wherein the pharmaceutical composition is administered in an amount sufficient to prevent the intact ocular surface from disruption, and wherein said isolated fragment of clusterin is administered in an amount sufficient to inhibit TNF-alpha induction of MMP-9 and bind and inhibit the activity of MMP-9.

2. The method of claim 1, wherein the pharmaceutical composition comprises secreted clusterin.

3. The method of claim 1, wherein the pharmaceutical composition is administered topically as a drop.

4. The method of claim 1, wherein the pharmaceutical composition further comprises a liquid carrier, and administration is by contacting the pharmaceutical composition to the surface of an eye of the patient.

5. The method of claim 1, wherein the pharmaceutical composition further comprises a carrier.

6. The method of claim 5, wherein the pharmaceutical composition is a sterile solution.

7. The method of claim 6, wherein the pharmaceutical composition is administered topically as a drop.

* * * * *

UNITED STATES PATENT AND TRADEMARK OFFICE
CERTIFICATE OF CORRECTION

| | |
|---|---|
| PATENT NO. | : 10,398,755 B2 |
| APPLICATION NO. | : 14/971862 |
| DATED | : September 3, 2019 |
| INVENTOR(S) | : M. Elizabeth Fini and Shinwu Jeong |

It is certified that error appears in the above-identified patent and that said Letters Patent is hereby corrected as shown below:

In the Specification

Column 1, Lines 18-21:
This invention was made with government support under Contract Nos. R01 EY12651, R01 EY09828, P30 EY14801, and P30 EY03040 awarded by the National Institutes of Health. The government has certain rights in the invention.

Should read as follows:
This invention was made with government support under EY014801, EY009828, EY012651, and EY003040 awarded by the National Institutes of Health. The government has certain rights in the invention.

Signed and Sealed this
Twenty-eighth Day of February, 2023

Katherine Kelly Vidal
*Director of the United States Patent and Trademark Office*